US011832812B2

(12) United States Patent
Rousseau

(10) Patent No.: US 11,832,812 B2
(45) Date of Patent: Dec. 5, 2023

(54) SYSTEMS, DEVICES AND METHODS OF MAKING SURGICAL SUTURES HAVING REFORMED, REDUCED DIAMETER, OFFSET TIPS

(71) Applicant: Ethicon, Inc., Raritan, NJ (US)

(72) Inventor: Robert A. Rousseau, Ottsville, PA (US)

(73) Assignee: Ethicon, Inc., Raritan, NJ (US)

( * ) Notice: Subject to any disclaimer, the term of this patent is extended or adjusted under 35 U.S.C. 154(b) by 169 days.

(21) Appl. No.: 17/551,788

(22) Filed: Dec. 15, 2021

(65) Prior Publication Data

US 2022/0104812 A1  Apr. 7, 2022

Related U.S. Application Data

(62) Division of application No. 16/203,113, filed on Nov. 28, 2018, now Pat. No. 11,224,421.

(51) Int. Cl.
*A61B 17/06* (2006.01)
*A61B 17/00* (2006.01)
(Continued)

(52) U.S. Cl.
CPC .. *A61B 17/06195* (2013.01); *A61B 17/06166* (2013.01); *A61B 2017/00526* (2013.01);
(Continued)

(58) Field of Classification Search
CPC ........ A61B 17/06166; A61B 17/06195; A61B 2017/00526; A61B 2017/0053
See application file for complete search history.

(56) References Cited

U.S. PATENT DOCUMENTS 3,534,740 A  10/1970  Thompson
3,890,975 A   6/1975  McGregor
(Continued)

FOREIGN PATENT DOCUMENTS

FR  2687565      8/1993
WO  03070453     8/2003
WO  2013085880   6/2013

OTHER PUBLICATIONS

International Search Report issued in corresponding International Application No. PCT/IB2019/059990, dated Apr. 21, 2020, 6 pages.

*Primary Examiner* — Phong Son H Dang

(57) ABSTRACT

A system for making a surgical suture having a reformed tip includes a receiver die having a top surface, a bottom surface, and an elongated channel formed in the top surface that extends between first and second ends of said receiver die. The elongated channel includes a suture channel having a first end and a second end, a first sloping surface that extends downwardly between the first end of the suture channel and the first end of the receiver die, and a second sloping surface that extends downwardly between the second end of the suture channel and the second end of the receiver die. The system includes an upper die having a top surface and a bottom surface that opposes the top surface of the receiver die. The system has an open die position in which the bottom surface of the upper die is spaced away from the top surface of the receiver die and a closed die position in which the bottom surface of the upper die is in contact with the top surface of the receiver die. A cutting element is coupled with the receiver die and the upper die.

10 Claims, 21 Drawing Sheets

(51) Int. Cl.
*D02J 1/04* (2006.01)
*D02J 1/18* (2006.01)

(52) U.S. Cl.
CPC . *D02J 1/04* (2013.01); *D02J 1/18* (2013.01); *D10B 2509/04* (2013.01)

(56) References Cited

U.S. PATENT DOCUMENTS

| | | |
|---|---|---|
| 3,926,194 A | 12/1975 | Greenberg et al. |
| 4,027,519 A | 6/1977 | Bachle |
| 4,557,264 A | 12/1985 | Hinsch |
| 4,832,025 A | 5/1989 | Coates |
| 5,007,922 A | 4/1991 | Chen et al. |
| 5,080,667 A | 1/1992 | Chen et al. |
| 5,156,788 A | 10/1992 | Chesterfield et al. |
| 5,180,385 A | 1/1993 | Sontag |
| 5,201,760 A | 4/1993 | West |
| 5,207,701 A | 5/1993 | West |
| 5,224,955 A | 7/1993 | West |
| 5,236,443 A | 8/1993 | Sontag |
| 5,258,014 A | 11/1993 | Harada et al. |
| 5,269,808 A * | 12/1993 | Proto ............... A61B 17/06195 606/228 |
| 5,358,498 A | 10/1994 | Shave |
| 5,415,707 A | 5/1995 | Bendel et al. |
| 5,507,777 A * | 4/1996 | Kus ................. A61B 17/06166 606/228 |
| 5,643,628 A * | 7/1997 | Sonderegger ............ B05D 7/20 427/398.1 |
| 5,707,391 A | 1/1998 | Carpentieri |
| 5,891,166 A * | 4/1999 | Schervinsky ....... B29C 66/8122 606/228 |
| 6,730,111 B2 | 5/2004 | Shchervinsky |
| 7,347,813 B2 | 3/2008 | Claren et al. |
| 8,056,599 B2 * | 11/2011 | Maiorino .......... A61B 17/06166 156/73.2 |
| 8,062,437 B2 | 11/2011 | Cichocki et al. |
| 8,216,497 B2 | 7/2012 | Lindh et al. |
| 8,641,732 B1 | 2/2014 | Goraltchouk et al. |
| 8,778,102 B2 * | 7/2014 | Maurer ................ B23K 26/389 148/668 |
| 8,961,560 B2 | 2/2015 | Avelar et al. |
| 9,358,000 B2 | 6/2016 | Cichocki et al. |
| 9,687,227 B2 | 6/2017 | Marczyk et al. |
| 9,770,241 B2 | 9/2017 | Rousseau et al. |
| 10,478,178 B2 | 11/2019 | Rousseau et al. |
| 10,835,238 B2 * | 11/2020 | Marczyk .......... A61B 17/06166 |
| 2003/0041426 A1 | 3/2003 | Genova et al. |
| 2005/0119696 A1 | 6/2005 | Walters et al. |
| 2006/0030883 A1 | 2/2006 | Cichocki |
| 2008/0147118 A1 | 6/2008 | Cichocki |
| 2008/0300552 A1 | 12/2008 | Cichocki |
| 2009/0259252 A1 * | 10/2009 | Kennedy .......... A61B 17/06166 606/228 |
| 2009/0312720 A1 | 12/2009 | Mauer |
| 2010/0139883 A1 | 6/2010 | Stametz et al. |
| 2013/0150872 A1 | 6/2013 | Rousseau |
| 2015/0351752 A1 | 12/2015 | Rousseau et al. |

\* cited by examiner

SYSTEMS, DEVICES AND METHODS OF MAKING SURGICAL SUTURES HAVING REFORMED, REDUCED DIAMETER, OFFSET TIPS

CROSS-REFERENCE TO RELATED APPLICATIONS

The present patent application is a divisional application of U.S. patent application Ser. No. 16/203,113, filed on Nov. 28, 2018, published as US 2020/0163669, now allowed, the disclosure of which is hereby incorporated by reference herein.

BACKGROUND OF THE INVENTION

Field of the Invention

The present patent application is generally related to surgical sutures, and is more specifically related to systems, devices and methods for tipping surgical sutures.

Description of the Related Art

Many surgical procedures use a combination of a surgical needle and a suture attached to the needle to close wounds and/or approximate tissue. In the past, most surgical needles had an eye located at the proximal end of the needle through which a surgical suture could be passed for attaching the suture to the proximal end of the needle. This design required the proximal end of the needle to have a sufficient size to allow for the eye to be formed at the proximal end to accommodate at least the maximum diameter of a suture strand to be folded around the eye. The doubling of the maximum diameter of the suture and the requisite increased size of the proximal end of the needle resulted in a needle-suture combination having a large cross-sectional area as it was passed through tissue. The resulting hole, produced when the needle-suture combination passed through the tissue, was substantially greater than the cross-sectional area of the trailing suture used to approximate the tissue.

Over the years, in order to improve surgical procedures and patient outcomes, various techniques have been developed to eliminate the eye located at the proximal end of the needle and to find other techniques and methods by which a suture strand could be attached to the proximal end of a surgical needle. For example, one improved suture attachment technique involves forming a channel in the proximal end of a needle by a conventional metal forming process. In this technique, the distal end of the suture is placed in the channel and the channel is mechanically swaged to mechanically secure the suture end in the needle channel. Another known technique involves drilling a bore hole into the proximal end of a surgical needle using conventional processes such as laser drilling and mechanical drilling. In a similar manner, the distal end of a surgical suture is placed into the bore hole and the proximal end of the needle containing the bore hole is mechanically swaged. Many of these techniques required the diameter or maximum dimension of the proximal end of a needle to be substantially larger than the diameter of the elongated body of an attached suture, and hence when such needle-suture combinations are used to join tissue, the suture still does not completely fill the resulting hole and pathway in tissue formed by the needle.

There have been many efforts directed to providing improved surgical needle-suture combinations. For example, U.S. Pat. No. 3,890,975 to McGregor discloses a braided suture that is subjected to sizing through the application of tension when dipped in a liquid resin solution. The suture is dried to remove the solvent and to allow the coated region to solidify. Since the braided suture is subjected to tension, there is a reduction in diameter as the braided elements begin to align axially thereby compacting the core fibers. As the liquid resin dries, the coated region or tip of suture containing the tensioned coated fibers is locked into the reduced diameter configuration. The uncoated region resumes the original diameter when the tension is released. The sizing operation is conducted to ensure that the suture will release at a more consistent force from the needle after crimping. This process is only applicable to braided sutures, and the final suture diameter is dependent upon the quality or density of the braided suture utilized.

U.S. Pat. No. 4,832,025 to Coates discloses a method for treating braided sutures that involves melt fusion of the tip region for insertion into a surgical needle. The suture is heated to an elevated temperature sufficient to effectively "melt fuse" a portion of the outer filaments of the multifilament suture. Such temperatures are typically in the range of about 260° C. to 300° C. (500° F. to 572° F.). The suture then stiffens upon cooling. Surface melting of the outer filaments has the effect of holding the filaments together when the suture is cut. It also causes stiffening of the suture which facilitates insertion of the suture end into the drilled bore hole of a needle. However, this melt fusion process has several significant drawbacks. Firstly, the melt fusion of filaments weakens the suture, whose tensile strength is degraded in proportion to the extent of melt fusion. Secondly, melt fusion causes an irreversible change in the suture filaments, which results in permanent stiffening and significant loss of the outer braided sheath tensile strength; and, this may result in sheaths that fracture and release independent of the core fibers causing bunching of the suture sheath during use.

U.S. Pat. No. 5,007,922 to Chen et al. discloses a method of producing monofilament sutures with regions of reduced diameter suture. The suture is wound in a helical or spiral configuration about a drum unit. The drum unit contains a region that is capable of expanding to produce an effectively larger perimeter dimension about the drum through the use of a split drum design. Once the fiber is wound about the perimeter of the drum, a heating element is positioned against the side of the drum tangentially along an axis that is parallel to the central axis of the drum. The heating element increases the temperature of any suture that is exposed along this line of contact along the side of the drum. After a satisfactory amount of heating has occurred, the drum is actuated such that the perimeter of the drum is increased. Since the suture is wound about the perimeter of the drum, the regions of heated suture are drawn down to accommodate the change in this dimension. This process results in reduced diameter regions within the suture that are highly oriented, beyond the orientation of the remaining non-heated regions of the suture. In addition to the change in molecular alignment, the resultant suture diameters of the exposed regions will vary depending upon the amount of deformation experienced in either overheated or underheated segments of fiber windings.

U.S. Pat. No. 8,216,497 to Lindh et al. discloses various methods for forming tissue holding devices having predetermined shapes suitable for use in surgical applications, and devices formed in accordance with such methods are also provided. These methods include press-forming methods, and press-forming methods in combination with profile punching. Tissue holding devices formed in accordance with such methods include various configurations for a core and a plurality of tissue holding elements, such as barbs, extending outwardly from the core. The processes provide a method to shape an extruded fiber, at an elevated temperature, into a broader configuration that enables punch press-type technology to be applied to remove sections of the formed fiber component to form solid barbed elements. Their intention is to maintain a center region that is closer to the cross-sectional area of a traditional suture with appendages essentially extending from this core. Since the cross-sectional area of the core of the fiber is sized to be equivalent to a comparative non-barbed suture, the strength is essentially the same as the traditional comparative fiber. The process, as disclosed, relies on the displacement of the entire length of fiber to produce a uniform billet that is to be subjected to punching of the fiber. The punching operation produces a fiber with an oval configuration with extensions from a central core region to ensure that the fiber meets the knot tensile strength requirements for a comparably sized round suture. Due to the large displacement of the entire fiber volume to create a pre-punch billet, the straight tensile strength of the suture body is reduced relative to an unformed extruded suture because of the loss of orientation in the bulk forming process. Additionally, due to the reliance of bulk billet production, the process of forming and cutting cannot be linked into a continuous form and cut process due to the space required for said production.

Many of the above-identified methodologies produce multi-diameter sutures, wherein the body of the suture is substantially larger than the portion of the suture (e.g., the tip) that is attached or mounted to a non-eyed needle, either in a channel or bore hole. The processes for producing reduced diameter suture tips typically alter the flexibility of the suture in the reduced sections in a negative manner by causing an increase in fiber stiffness or a loss of suture diameter consistency, thereby producing variable needle attachment strength.

Although the suture tipping processes of the prior art are adequate for their intended purpose, there are certain deficiencies attendant with their use. The deficiencies include loss of flexibility of the suture in the tipped region, fibrillation of the tipped region, alteration of the suture material yield stress, variability in finished tip geometry and limited applicability to non-braided sutures as well as reliance on delicate tooling.

Thus, there remains a need for surgical needle-suture combinations whereby the maximum diameter of the needle and the maximum diameter of the suture is the same size so that a hole and pathway in tissue resulting from a surgeon passing the needle through the tissue during a surgical procedure is substantially filled by the body of the suture. This requirement is especially important when joining or approximating highly vascularized tissue in order to prevent oozing or seepage of blood through the pathway and hole produced by the needle. This requirement is also important for closing off pathways for bacteria to prevent infections.

Moreover, there remains a need for improved systems, devices and methods for producing sutures having reformed tips with reduced cross-sectional areas that maintain the suture material properties of yield stress and suture flexibility at the needle attachment location, while providing consistent needle attachment strength through improved suture tip physical dimensions. There also remains a need for improved systems, devices and methods for making monofilament sutures having novel tip structures or sections that overcome the disadvantages found in the prior art.

SUMMARY OF THE INVENTION

In one embodiment, a method of making a surgical suture having a reformed tip preferably includes providing an elongated fiber having a first end, a second end, a central axis extending between the first and second ends thereof, and an outer surface that defines a cross-sectional dimension of the elongated fiber, and compressing a center region of the elongated fiber that is located between the first and second ends thereof for reshaping the center region into a core mass and a deformed mass that extends laterally outside the cross-sectional dimension of the elongated fiber.

In one embodiment desirably includes separating the deformed mass of the center region from the core mass of the center region so that only the core mass remains for interconnecting the first and second ends of the elongated fiber, and after separating the deformed mass from the core mass, reshaping the core mass into a reformed mass having a reformed mass central axis that is offset from the central axis of the elongated fiber.

In one embodiment, the step of compressing the center region of the elongated fiber preferably includes using a die for compressing at least two sides of the outer surface of the elongated fiber.

In one embodiment, the step of compressing the center region of the elongated fiber may include using a die for constraining at least three sides of the center region of the elongated fiber for forming the core mass while not constraining one side of the elongated fiber for forming the deformed mass.

In one embodiment, the step of using the die for compressing at least two sides of the elongated fiber desirably includes providing a receiver die having a top surface and an elongated channel formed in the top surface, providing an upper die having a bottom surface that opposes the top surface of the receiver die, and with the bottom surface of the upper die spaced away from the top surface of the receiver die, positioning the center region of the elongated fiber within the elongated channel of the receiver die. In one embodiment, the method preferably includes moving the bottom surface of the upper die into contact with the top surface of the receiver die for compressing the center region of the elongated fiber between the upper die and the receiver die.

In one embodiment, the deformed mass may be separated from the core mass by cutting the deformed mass from the core mass. In one embodiment, the deformed mass may be cut from the core mass by using a cutting element having a sharpened cutting blade for cutting the deformed mass from the core mass.

In one embodiment, reshaping the core mass may include after cutting the deformed mass from the core mass, moving the upper die away from the receiver die to provide a gap between the bottom surface of the upper die and the top surface of the receiver die, and advancing first and second reforming dies into the gap between the bottom surface of the upper die and the top surface of the receiver die to engage the core mass for reshaping the core mass from a post-cut shape to a reformed shape that is different than the post-cut shape.

In one embodiment, the first reforming die may include a first J-shaped structure having a first concave curved surface, and the second reforming die may include a second J-shaped structure having a second concave curved surface.

In one embodiment, the method may include heating the elongated fiber. In one embodiment, the elongated fiber may include a biocompatible polymer.

In one embodiment, a system for making a surgical suture having a reformed tip may include a receiver die having a top surface, a bottom surface, and an elongated channel formed in the top surface that extends between first and second ends of the receiver die. In one embodiment, the elongated channel preferably includes a suture channel having a first end and a second end, a first sloping surface that extends downwardly between the first end of the suture channel and the first end of the receiver die, and a second sloping surface that extends downwardly between the second end of the suture channel and the second end of the receiver die.

In one embodiment, a system for making a surgical suture having a reformed tip preferably includes an upper die having a top surface and a bottom surface that opposes the top surface of the receiver die. In one embodiment, the system desirably has an open die position in which the bottom surface of the upper die is spaced away from the top surface of the receiver die and a closed die position in which the bottom surface of the upper die is in contact with the top surface of the receiver die.

In one embodiment, the system may include a cutting element coupled with the receiver die and the upper die. In one embodiment, the system may have a cutting element guide slot that extends through the upper die and the receiver die along a cutting element movement axis that crosses the bottom surface of the upper die and the top surface of the receiver die. In one embodiment, the cutting element is preferably adapted to slide within the cutting element movement axis of the cutting element guide slot in a first direction toward the top surface of the upper die and in a second direction toward the bottom surface of the receiver die.

In one embodiment, the suture channel located within the receiver die preferably includes a suture seating surface that extends in a plane that is parallel with the top surface of the receiver die. In one embodiment, the first sloping surface preferably slopes downwardly between the first end of the suture channel and the bottom surface of the receiver die. In one embodiment, the second sloping surface preferably slopes downwardly between the second end of the suture channel and the bottom surface of the receiver die.

In one embodiment, the cutting element may have an upper end, a lower end, a sharpened cutting edge located between the upper and lower ends of the cutting element, and first and second guide legs located on opposite ends of the sharpened cutting edge. The guide legs of the cutting element preferably pass through the cutting element guide slot for guiding the sliding movement of the cutting element.

In one embodiment, the system may include a suture reforming assembly including first and second reforming die having an extended position in which the first and second reforming die are joined together between the first and second guide legs of the cutting element for reshaping a core mass of an elongated fiber and a retracted position in which the first and second reforming die are spaced from one another.

In one embodiment, a surgical suture having an off-axis distal tip preferably includes an elongated fiber, such as an elongated fiber made of a biocompatible polymer material, having a proximal end, a distal end, a central axis extending between the proximal and distal ends thereof, and a first outer surface defining a first cross-sectional dimension. In one embodiment, the elongated fiber preferably includes a distal tip located at the distal end thereof, the distal tip having a second outer surface that defines a second cross-sectional dimension that is smaller than the first cross-sectional dimension of the first outer surface. In one embodiment, the distal tip preferably has a central axis that is offset from the central axis of the elongated fiber.

In one embodiment, a portion of the second outer surface of the distal tip may be aligned with a portion of the first outer surface of the elongated fiber.

In one embodiment, the elongated fiber may include a sloping transition surface that extends between the first outer surface of the elongated fiber and the second outer surface of the distal tip.

In one embodiment, a system for making a surgical suture having a reformed, reduced diameter distal tip preferably includes a first roller having a first groove formed therein that extends around the outer perimeter of the first roller, and a second roller opposing the first roller, the second roller having a second groove formed therein that extends around the outer perimeter of the second roller.

In one embodiment, a system desirably includes a drive system for bringing the first and second rollers together for contacting opposite sides of an elongated fiber and compressing the elongated fiber between the outer perimeters of the respective first and second rollers as the first and second rollers are driven over a section of the elongated fiber for reforming the section of the elongated fiber into a core mass of the elongated fiber and at least one deformed mass of the elongated fiber.

In one embodiment, a system preferably includes a cutting element for cutting the at least one deformed mass of the elongated fiber from the core mass of the elongated fiber so that only the core mass of the elongated fiber remains for interconnecting first and second ends of the elongated fiber.

In one embodiment, a system preferably includes a suture reforming assembly having first and second reforming die that move between an extended position in which opposing faces of the first and second reforming die engage opposite sides of the core mass for reshaping the core mass and a retracted position in which the first and second reforming die are spaced away from one another and not in contact with the opposite sides of the core mass.

In one embodiment, the present patent application discloses systems, devices and methods that involve a single sided formation and trimming of an elongated fiber, coupled with a secondary reforming operation, for enabling the use of larger robust tooling.

In one embodiment, the systems, devices and methods disclosed herein may be used to manufacture a needle-suture combination, which when used to join tissue, results in the hole produced by the needle being substantially filled by the monofilament suture joining the tissue.

In one embodiment, the systems, devices and methods disclosed herein may be used to manufacture a novel suture tip section on a monofilament suture.

In one embodiment, the systems, devices and methods disclosed herein may be used to manufacture a suture having a tip with a novel offset axis and/or asymmetrical form.

In one embodiment, the systems, devices and methods disclosed herein may be used to manufacture a novel tip section on a monofilament suture.

In one embodiment, the systems, devices and methods disclosed herein may be used to manufacture a surgical suture having a reduced cross-sectional area portion from monofilaments of various polymeric or ductile materials. In one embodiment, a monofilament is subjected to the application of mechanical shaping of the fiber element, optionally coupled with thermal treatment, to produce a deformed cross-sectional portion of the suture body. The deformed suture body region is subsequently subjected to a trimming operation within a punching or stamping die. The reduced section of the suture body region is severed to form a suture having a reduced cross-sectional area end portion. In one embodiment, each reduced region is severed approximately in the center of the trimmed reduced cross-sectional area portion to form a suture having both ends with a reduced cross-sectional area.

In one embodiment, a center region of a suture may be compressed to produce a center region having a flattened section. In one embodiment, at least a part of the flattened center region may be removed (e.g., cut) to provide a center region having a reduced cross-sectional area that is off-set from a central axis of the main body portion of the suture. The removing operation may be achieved by cutting, shearing, ultrasonic, thermal, laser ablation, or other energy based devices.

In one embodiment, the reduced cross-sectional area may be subjected to a second forming operation to provide a transition section and a tip section having a cross-section with an outer perimeter, whereby the maximum dimension of the cross-section of the tip section is less than the maximum cross-sectional dimension of the suture body.

In one embodiment, the reduced cross-sectional area may be subjected to a second forming operation to provide a tip section that has a cross-sectional shape similar to that of the suture body.

In one embodiment, the reduced cross-sectional area that is cut may result in the formation of a tip section that is adapted and/or configured for insertion into a bore or opening at a proximal end of a surgical needle.

These and other preferred embodiments of the present patent application will be described in more detail below.

BRIEF DESCRIPTION OF THE DRAWINGS

FIG. 5B-1 shows a bottom view of the suture shown in FIG. 5B.

FIG. 5B-2 shows a side view of the suture shown in FIG. 5B.

FIG. 5B-3 shows a cross-sectional end view of the suture shown in FIG. 5B.

DETAILED DESCRIPTION OF PREFERRED EMBODIMENTS

Figure 1:
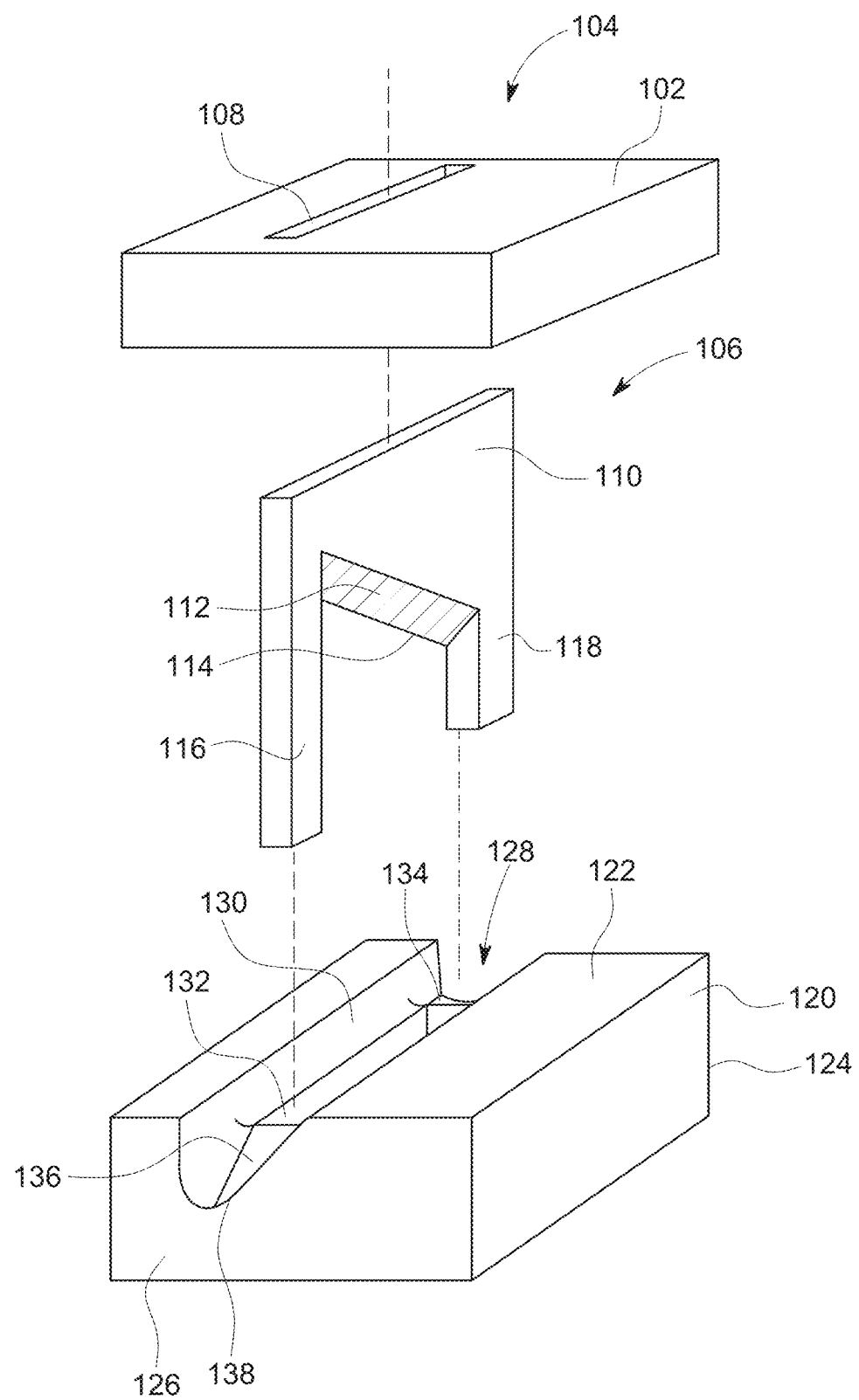
FIG. 1 shows an exploded view of a system for making sutures having reformed, reduced diameter tips including an upper die, a receiver die, and a cutting element, in accordance with one embodiment of the present patent application.

Referring to FIG. 1, in one embodiment, a system for making sutures having reformed, reduced diameter tips preferably includes an upper die 102 having a top surface 104 and a bottom surface 106. In one embodiment, the upper die desirably includes a first cutting element guide slot 108 that extends from the top surface 104 to the bottom surface 106 of the upper die.

In one embodiment, the system 100 preferably includes a cutting element 110 with an angled blade 112 having a sharpened cutting edge 114 that extends between first and second cutting element guide legs 116, 118 that extend to a lower end of the cutting element 110.

In one embodiment, the system 100 desirably includes a receiver die 120 that is adapted to receive a suture that will be cut and/or trimmed to form a suture having a reduced diameter tip. The receiver die 120 preferably has a top surface 122 that extends from a first end 124 to a second end 126 of the receiver die. In one embodiment, the receiver die 120 desirably includes an elongated channel 128 formed in the top surface 122 that extends from the first end 124 to the second end 126 of the receiver die. In one embodiment, the elongated channel 128 desirably includes a suture channel 130 that is adapted to seat a suture (e.g., a center region of a suture), whereupon the suture will be trimmed using the cutting element 110. The elongated channel 128 desirably includes a second cutting element guide slot 132 that is adapted to receive the first and second cutting element guide legs 116, 118 of the cutting element 110. In one embodiment, the first cutting element guide slot of the upper die and the second cutting element guide slot of the receiver die are preferably aligned with one another so that the cutting element may slide up and down within the upper die and the receiver die for cutting a laterally extending mass from a suture as part of a tip forming process.

In one embodiment, the receiver die 120 desirably includes a first sloping ramp 134 formed in the elongated channel 128, which is located at the first end 124 of the receiver die. The receiver die 120 preferably includes a second sloping ramp 136 formed in the elongated channel 128, which is located adjacent the second end 126 of the receiver die. In one embodiment, when a center region of a suture is positioned atop the suture channel 130, the outer ends (e.g., first and second ends that bound the center region) of the suture that are not positioned within the suture channel 130 are free to slope down in the respective first and second sloping ramps 134, 136. A relief form 138 is preferably located at the outer ends of each of the respective sloping ramps 134, 136 for minimizing damage to the elongated body of the suture as the suture is passed through the elongated channel 128 of the receiver die 120.

Figure 2:
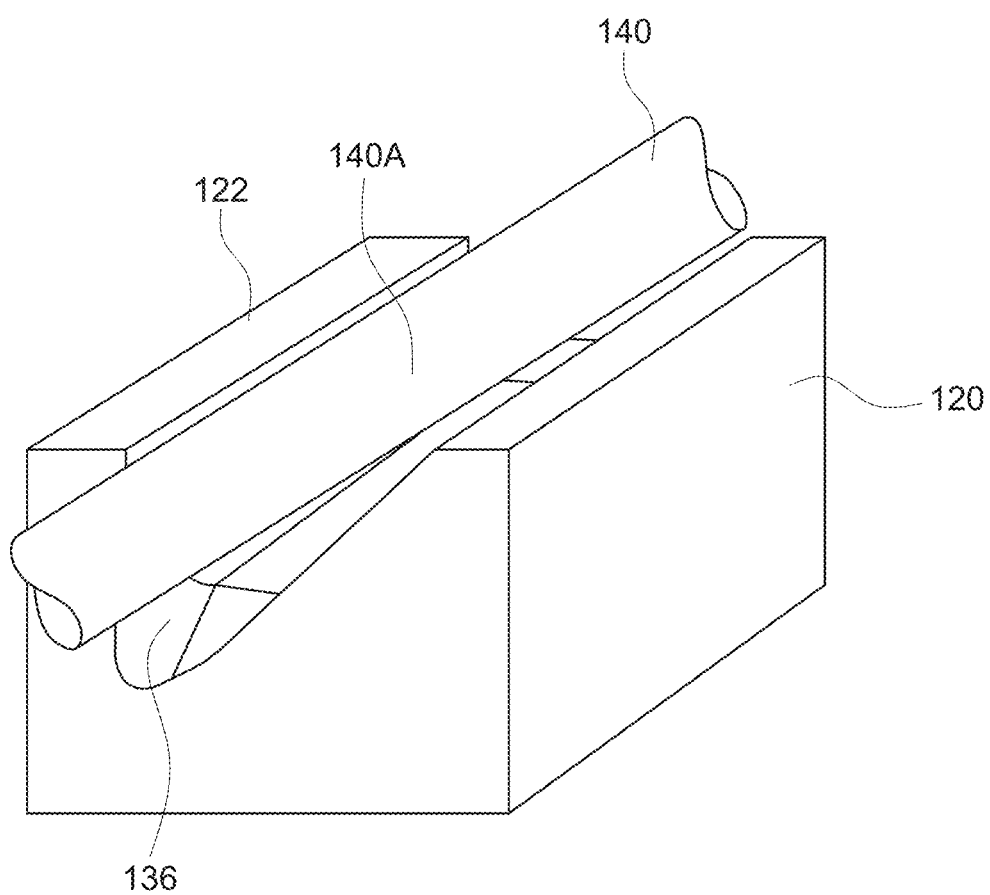
FIG. 2 shows a perspective view of the receiver die shown in FIG. 1.

Referring to FIG. 2, in one embodiment, in order to make a suture having a reformed, reduced diameter tip, a center region 140A of a suture 140 may be positioned atop the suture channel 130 (FIG. 1), which is preferably located within the elongated channel 128 formed in the top surface 122 of the receiver die 120. In one embodiment, the suture 140 is an elongated fiber that preferably extends along the longitudinal axis of the elongated channel 128 formed in the top surface 122 of the receiver die 120. The first and second ends 140B, 140C of the suture 140 that are not seated within the suture channel 130 (FIG. 1) are free to slope down over the first and second sloping ramps 134 (FIG. 1), 136 that are formed in the receiver die 120.

Figure 3A:
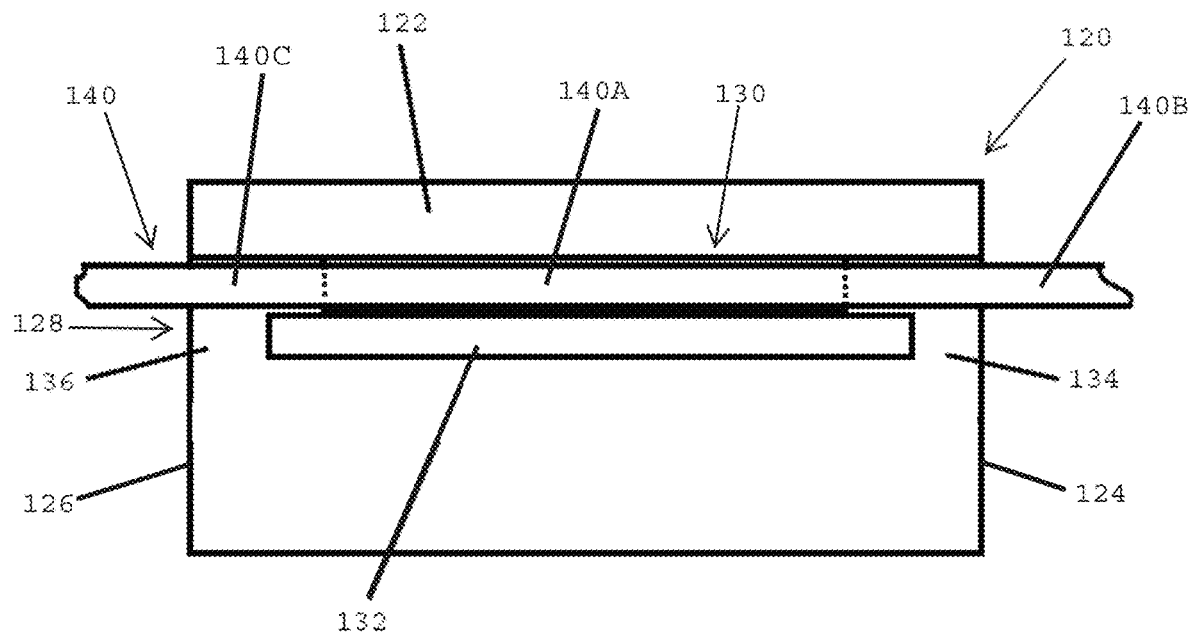
FIG. 3A shows a top plan view of the receiver die shown in FIG. 2.
Figure 3B:
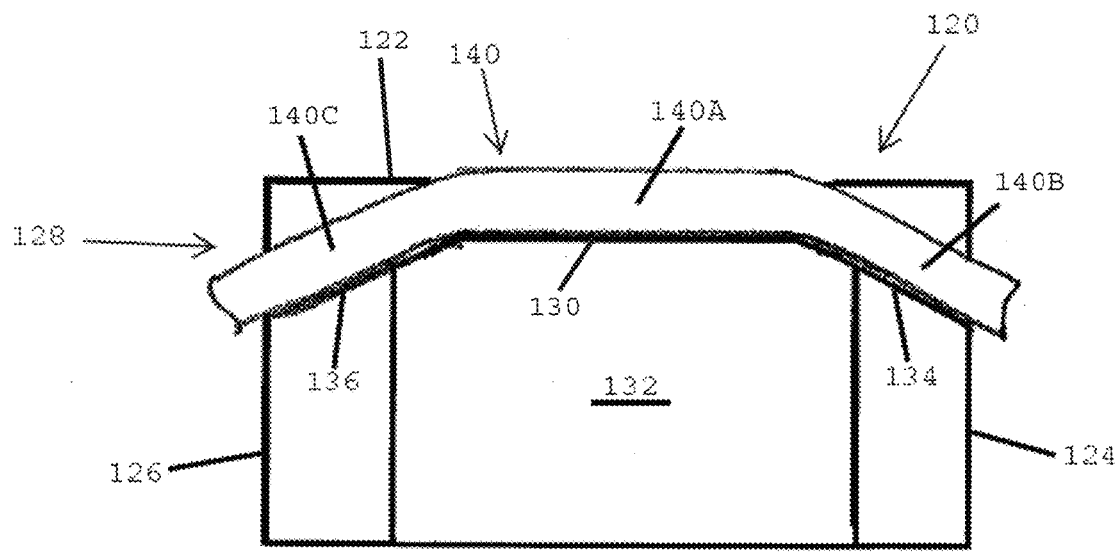
FIG. 3B shows a cross-sectional view of the receiver die shown in FIGS. 2 and 3A.

Referring to FIGS. 3A and 3B, in one embodiment, the receiver die 120 preferably has a top surface 122 with the elongated channel 128 formed in the top surface 122. In one embodiment, the elongated channel 128 preferably extends from the first end 124 to the second end 126 of the receiver die. The receiver die desirably includes the suture channel 130 that is adapted to seat a suture 140, such as a center region 140A of the suture, which will preferably be trimmed by the cutting element 110 (FIG. 1). In one embodiment, the suture channel 130 may include a suture supporting surface that is substantially flat and that is parallel with the top surface 122 of the receiver die 120. The suture supporting surface may seat the center region 140A of the suture, while enabling the first and second ends 140B, 140C of the suture to extend over the respective first and second sloping ramps 134, 136 of the receiver die.

In one embodiment, the receiver die 120 preferably includes the first sloping ramp 134 adjacent the first end 124 of the receiver die 120 and the second sloping ramp 136 adjacent the second end 126 of the receiver die 120. The first and second sloping ramps 134, 136 desirably slope down and away from the suture seating surface of the suture channel 130. When the suture 140 is positioned on the suture supporting surface of the suture channel 130, the first and second ends 140B, 140C of the suture may conform to the sloping surfaces of the respective first and second sloping ramps 134, 136.

In one embodiment, the receiver die 120 preferably includes the second cutting element guide slot 132 that is adapted to receive the cutting element guide legs 116, 118 and the sharpened cutting edge 114 of the cutting element 110 (FIG. 1) for guiding up and down movement of the cutting element. In one embodiment, the outer ends of the second cutting element guide slot are preferably aligned with the respective first and second sloping ramps 134, 136 of the receiver die.

Figure 4A:
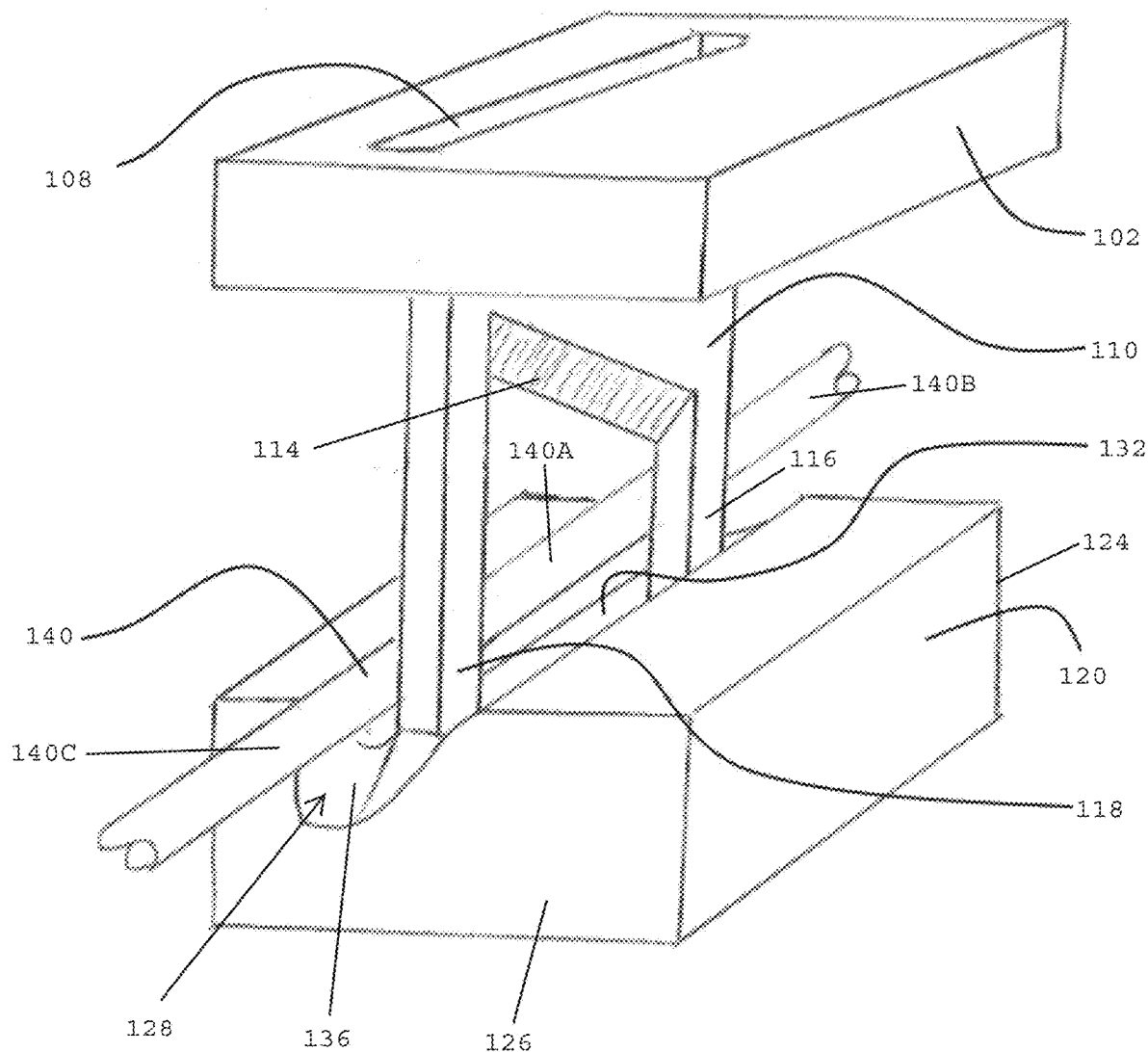
FIG. 4A shows a stage of a method of using the system shown in FIG. 1 for making a suture having a reformed, reduced diameter tip, in accordance with one embodiment of the present patent application.

Referring to FIG. 4A, in one embodiment, a suture 140 is preferably positioned within the suture channel 130 (FIG. 3B) formed in the elongated channel 128 of the receiver die 120. A center region 140A of the suture 140 that will be cut and/or trimmed is preferably aligned with the sharpened cutting edge 114 of the cutting element 110. The first and second ends 140B, 140C of the suture 140 are free to slope down over the respective first and second sloping ramps 134 (FIG. 3B), 136 adjacent the respective first and second ends 124, 126 of the receiver die 120. The first and second cutting element guide legs 116, 118 of the cutting element 110 are desirably inserted into the second cutting element guide slot 132 formed in the receiver die 120. The upper end of the cutting element 110 is preferably disposed within the first cutting element guide slot 108 provided in the upper die 102. In one embodiment, the first and second cutting element guide slots 108, 132 are desirably in alignment with one another when the upper die 102, the receiver die 120 and the cutting element 110 are assembled together for guiding sliding up and down movement of the cutting element during a suture cutting operation.

Figure 4B:
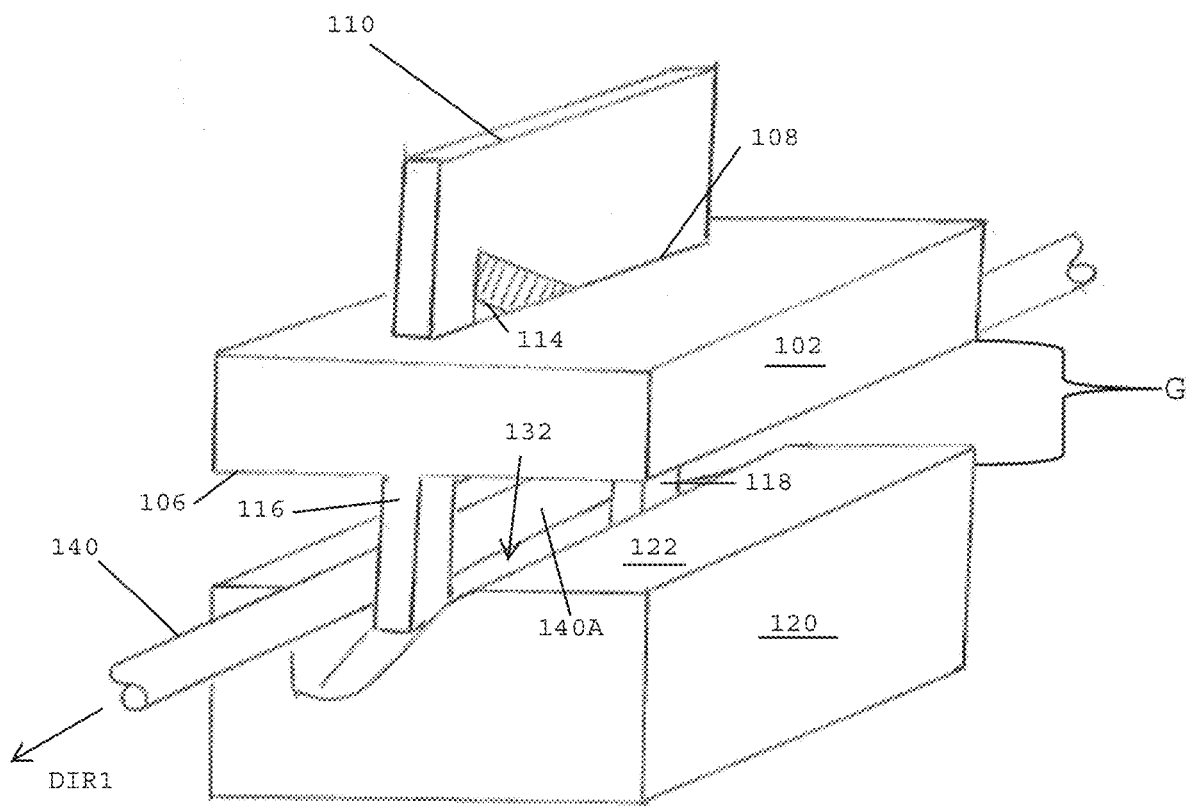
FIG. 4B shows a stage of a method of using the system shown in FIG. 1 for making a suture having a reformed, reduced diameter tip, in accordance with one embodiment of the present patent application.

Referring to FIG. 4B, in one embodiment, the upper die 102 may be spaced away from the receiver die 120 to define a gap G that extends from the bottom surface 106 of the upper die 102 and the top surface 122 of the lower die 120. The cutting element 110 is disposed in the first cutting element guide slot 108 provided in the upper die 102 with the first and second guide legs 116, 118 of the cutting element 110 disposed within the second cutting element guide slot 132 provided in the receiver die 120. In the open position shown in FIG. 4B, the suture 140 may pass freely between the bottom surface 106 of the upper die 102 and the top surface 122 of the receiver die 120 without contacting either the upper die 102 or the receiver die 120. In one embodiment, the suture 140 may be advanced in the direction DIR1 until the center region 140A of the suture 140 is aligned with the suture channel 130 (FIG. 1) of the receiver die 120, whereupon the center region 140A is positioned between the first and second cutting element guide legs 116, 118 of the cutting element 110. In this position, the center region 140A of the suture 140 is also in alignment with the sharpened cutting edge 114 of the cutting element 110 that extends between the first and second cutting element guide legs 116, 118.

Figure 4C:
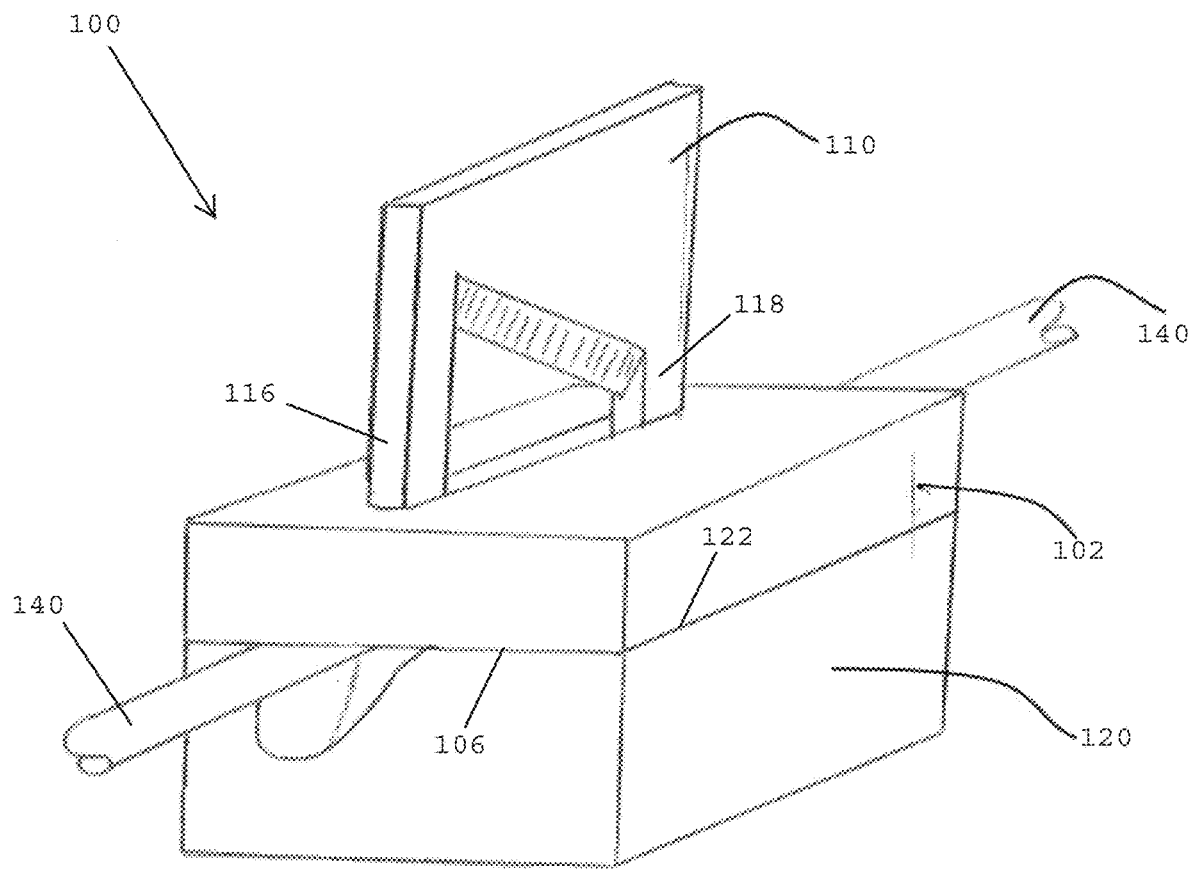
FIG. 4C shows a stage of a method of using the system shown in FIG. 1 for making a suture having a reformed, reduced diameter tip, in accordance with one embodiment of the present patent application.

Referring to FIG. 4C, in one embodiment, when an indexing operation for the suture 140 has been completed for properly aligning the suture relative to the upper die, the cutting element and the receiver die, the upper die 102 and the receiver die 120 are preferably brought into tight approximation so that the bottom surface 106 of the upper die 102 contacts the top surface 122 of the receiver die 120. In one embodiment, pressure is preferably applied through the upper die 102 and the receiver die 120 to cause the center region 140A (FIG. 4B) of the suture 140 to deform from its original extruded geometry whereupon a deformed mass of the center region extends laterally beyond the normal lateral surface of the elongated suture body. The center region of the suture that is deformed preferably occurs along the axis of the suture 140 that is positioned approximately in line with the space that is located between the first and second cutting element guide legs 116, 118 of the cutting element 110.

Figure 4D:
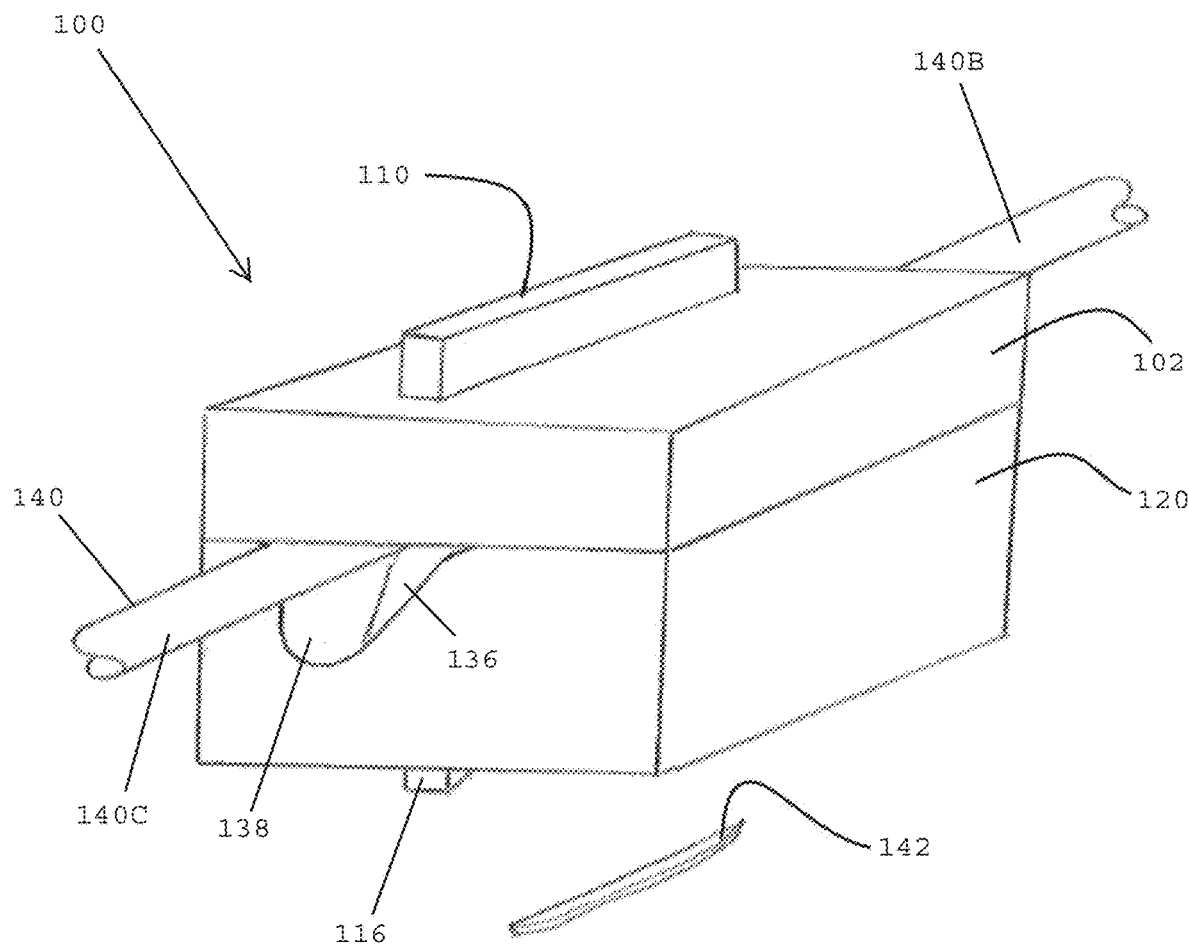
FIG. 4D shows a stage of a method of using the system shown in FIG. 1 for making a suture having a reformed, reduced diameter tip, in accordance with one embodiment of the present patent application.

Referring to FIG. 4D, in one embodiment, the cutting element 110 may be moved from an up position shown in FIG. 4C to a down position shown in FIG. 4D for cutting, trimming and/or shearing off a deformed mass of the suture that is located between the first cutting element guide leg 116 and the second cutting element guide leg 118 (FIG. 4C) of the cutting element 110. The cut portion of the deformed mass 142 is preferably removed as waste material. The first and second end portions 140B, 140C of the suture 140 that are aligned with the sloping end ramps of the receiver die 120 are preferably only compressed between the opposing faces of the upper die 102 and the sloping ramps for a portion of their total length. FIG. 4D shows the second sloping ramp 136 having the relief form 138.

Figure 5A:
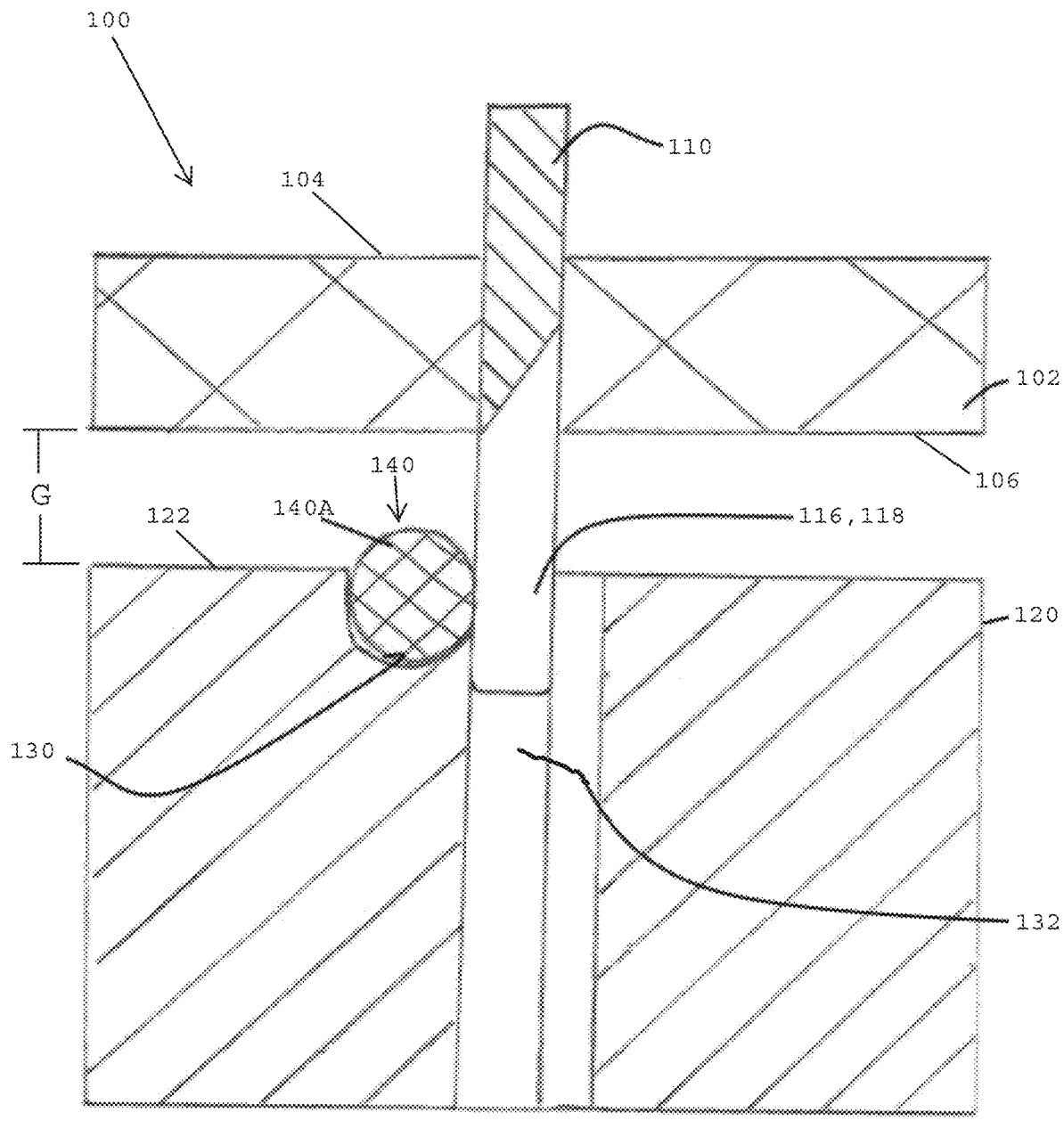
FIG. 5A shows a stage of a method of making a suture having a reformed, reduced diameter tip, in accordance with one embodiment of the present patent application.

Referring to FIG. 5A, in one embodiment, the center region 140A of the suture 140 is preferably positioned within the suture channel 130 of the receiver die 120. During one stage of a cutting operation, the upper die 102 is preferably spaced above the receiver die 120 so that a gap G exists between the bottom surface 106 of the upper die 102 and the top surface 122 of the receiver die 120. The first and second cutting element guide legs 116, 118 are desirably positioned within the second cutting element guide slot 132 of the receiver die 120 for guiding up and down movement of the cutting element 110. The upper end of the cutting element 110 is preferably disposed within the first cutting element guide slot 108 that extends from the top surface 104 to the bottom surface 106 of the upper die 102. When the upper die and the receiver dies are assembled together for cutting and/or trimming a suture, the first and second cutting element guide slots 108, 132 are preferably aligned with one another for guiding sliding up and down movement of the cutting element.

Figure 5B:
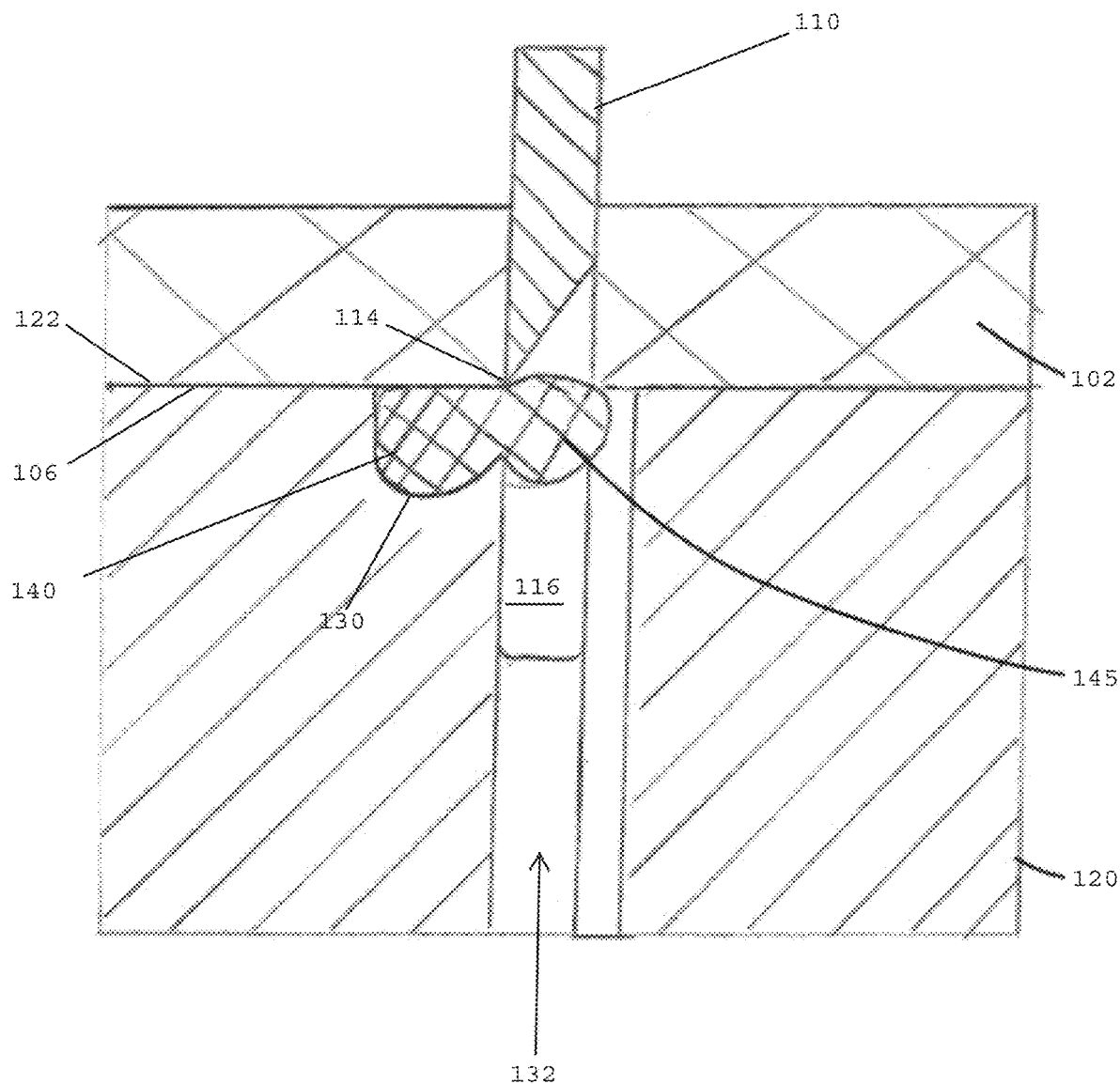
FIG. 5B shows a stage of a method of making a suture having a reformed, reduced diameter tip, in accordance with one embodiment of the present patent application.
Figures 1, 5B:
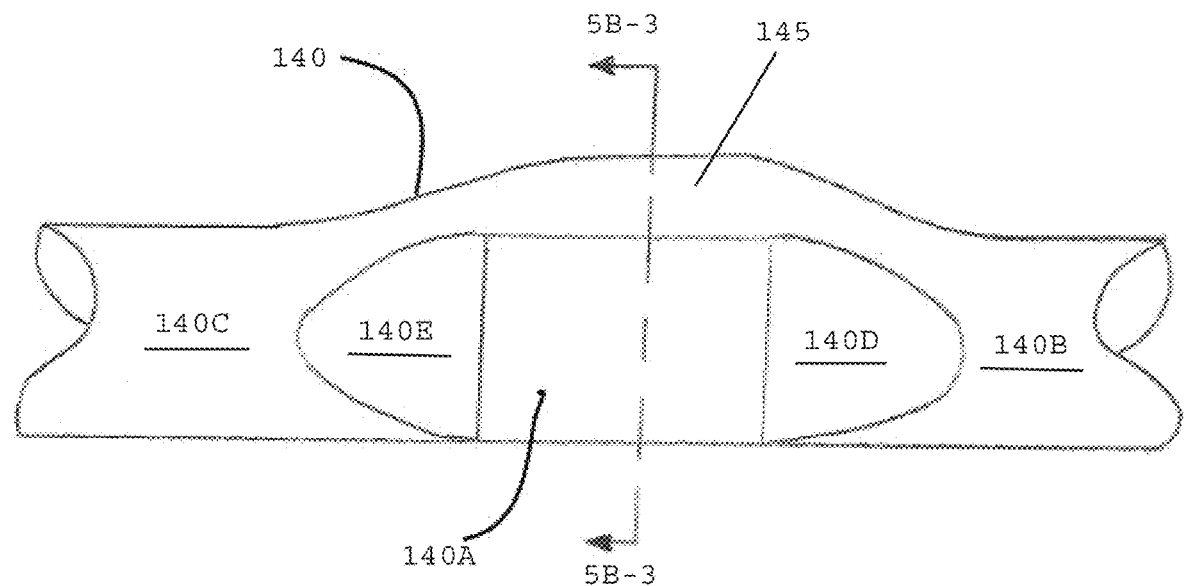
Figures 2, 5B:
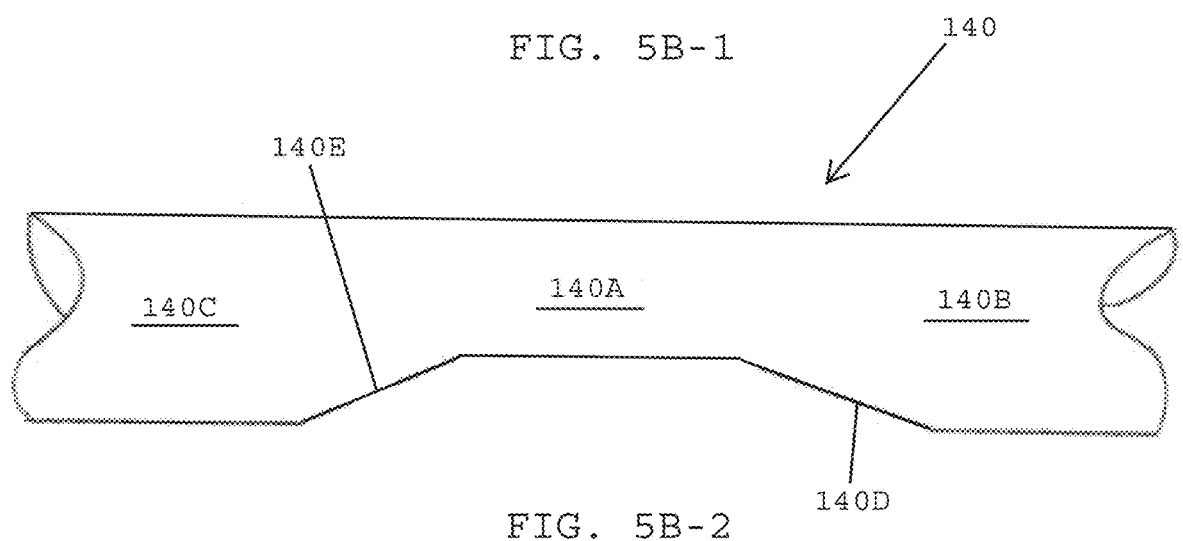
Figures 3, 5B:
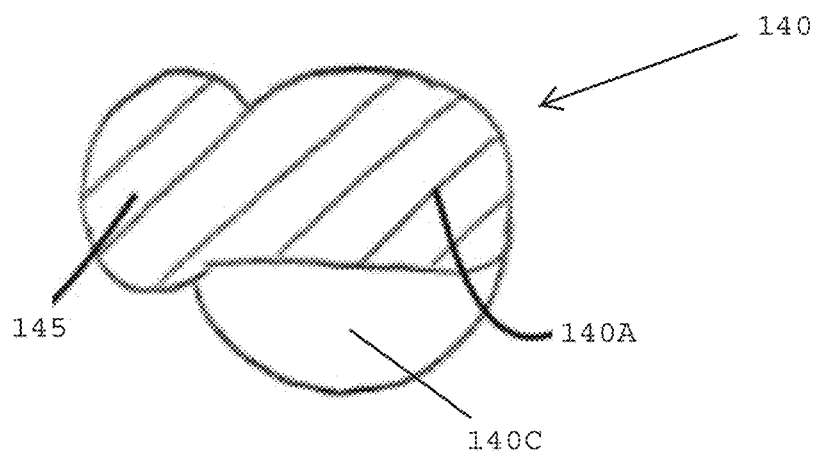

Referring to FIG. 5B, in one embodiment, the upper die 102 is closed onto the receiver die 120 so that the suture 140 is compressed between the bottom surface 106 of the upper die 102 and the suture channel 130 formed in the top surface 122 of the receiver die 120. The center region 140A (FIGS. 3A and 3B) of the suture 140 that is disposed within the suture channel 130 is deformed to provide a core mass 143 that remains within the bounds of the suture channel 130 and a deformed mass 145 that projects laterally between the first cutting element guide leg 116 and the second cutting element guide leg 118 of the cutting element 110. The sharpened cutting edge 114 of the cutting element 110 is desirably positioned between the core mass 143 of the suture 140 and the deformed mass 145 of the suture.

Referring to FIGS. 5B-1, 5B-2, and 5B-3, when the suture 140 is compressed between the upper die 102 and the receiver die 120 (FIG. 5B), the bottom surface of the center region 140A of the suture 140 that sits atop the suture channel 130 (FIG. 5B) is flattened and the first and second ends 140B, 140C of the suture that overlie the respective first and second sloping ramps 134, 136 (FIG. 3B) define sloping transition regions 140D, 140E of the suture that extend between the compressed, flattened center region and the uncompressed first and second ends 140B, 140C of the suture 140. As the center region 140A of the suture 140 is compressed, the deformed mass 145 of the suture projects laterally (relative to the longitudinal axis of the suture) into the first and second cutting element guide slots 108, 132 for being exposed to the sharpened cutting edge 114 of the cutting element 110.

Figure 5C:
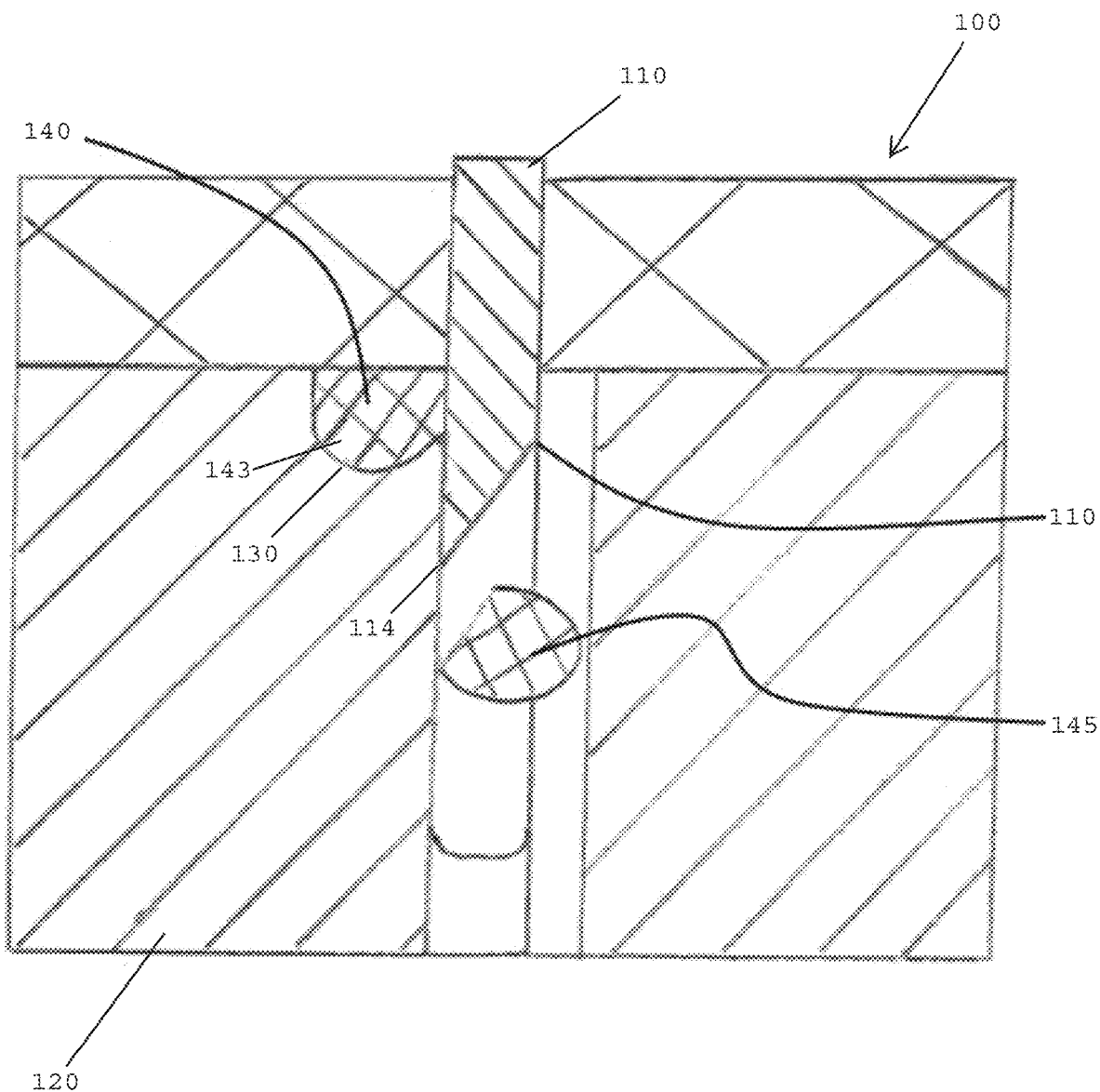
FIG. 5C shows a stage of a method of making a suture having a reformed, reduced diameter tip, in accordance with one embodiment of the present patent application.

Referring to FIG. 5C, in one embodiment, the cutting element 110 may be lowered down toward the bottom of the receiver die 120 whereupon the sharpened cutting edge 114 of the cutting element cuts the deformed mass 145 of the suture away from the core mass 143 of the suture. The remaining core mass 143 of the suture 140 has a reduced width relative to the uncut first and second ends 140B, 140C (FIG. 5B-2) of the suture. In one embodiment, after the deformed mass 145 has been cut away, it is removed from the system 100 as waste.

Figure 5D:
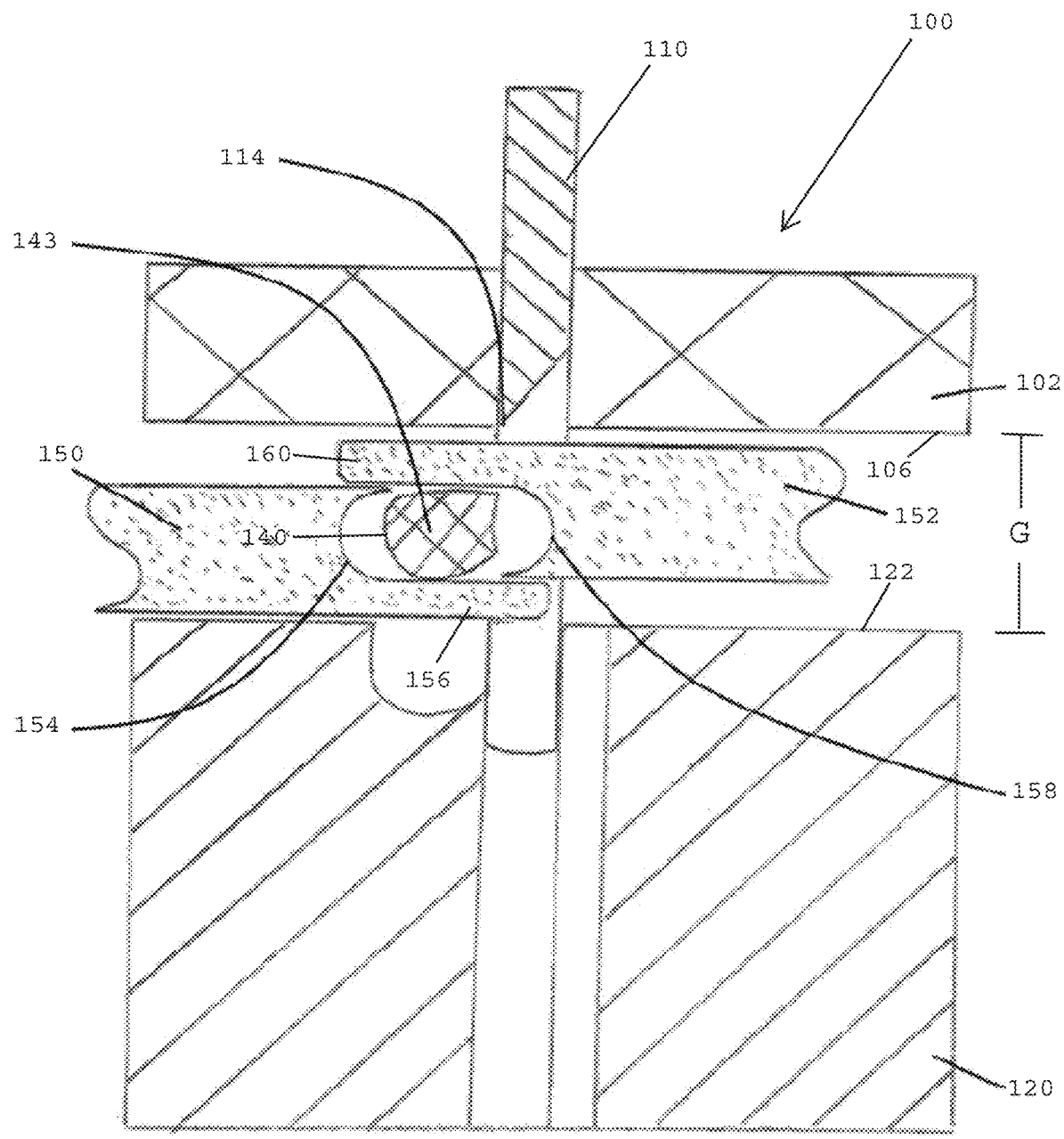
FIG. 5D shows a stage of a method of making a suture having a reformed, reduced diameter tip, in accordance with one embodiment of the present patent application.

Referring to FIG. 5D, in one embodiment, after the suture 140 has been cut by the cutting element 110, the core mass 143 remains for interconnecting the first and second ends of the suture. In one embodiment, the sharpened cutting edge 114 of the cutting element 110 is retracted, and the upper die 102 is preferably moved away from the receiver die 120 so that a gap G is once again present between the bottom surface 106 of the upper die 102 and the top surface 122 of the receiver die 120. As the upper die 102 moves away from the receiver die 120, the lateral access gap G may increase in size between the opposing faces of the upper die and the receiver die.

After the upper die 102 and the receiver die 120 have been moved away from one another to provide the lateral gap G therebetween, a reforming process may be performed on the core mass 143 utilizing first and second reforming dies 150, 152. In one embodiment, the first reforming die 150 has a concave curved surface 54 that includes a lower extension 156 to provide a J-shaped forming face. Similarly, the second reforming die 152 that opposes the first reforming die 150 has a concave curved surface 158 and an extension 160 that defines a J-shaped forming face. In one embodiment, the first and second reforming dies 150, 152 are adapted to move toward one another for pressing and reshaping the core mass 143 of the suture 140 to provide a reformed mass, which may have a cylindrical shaped outer profile.

Figure 5E:
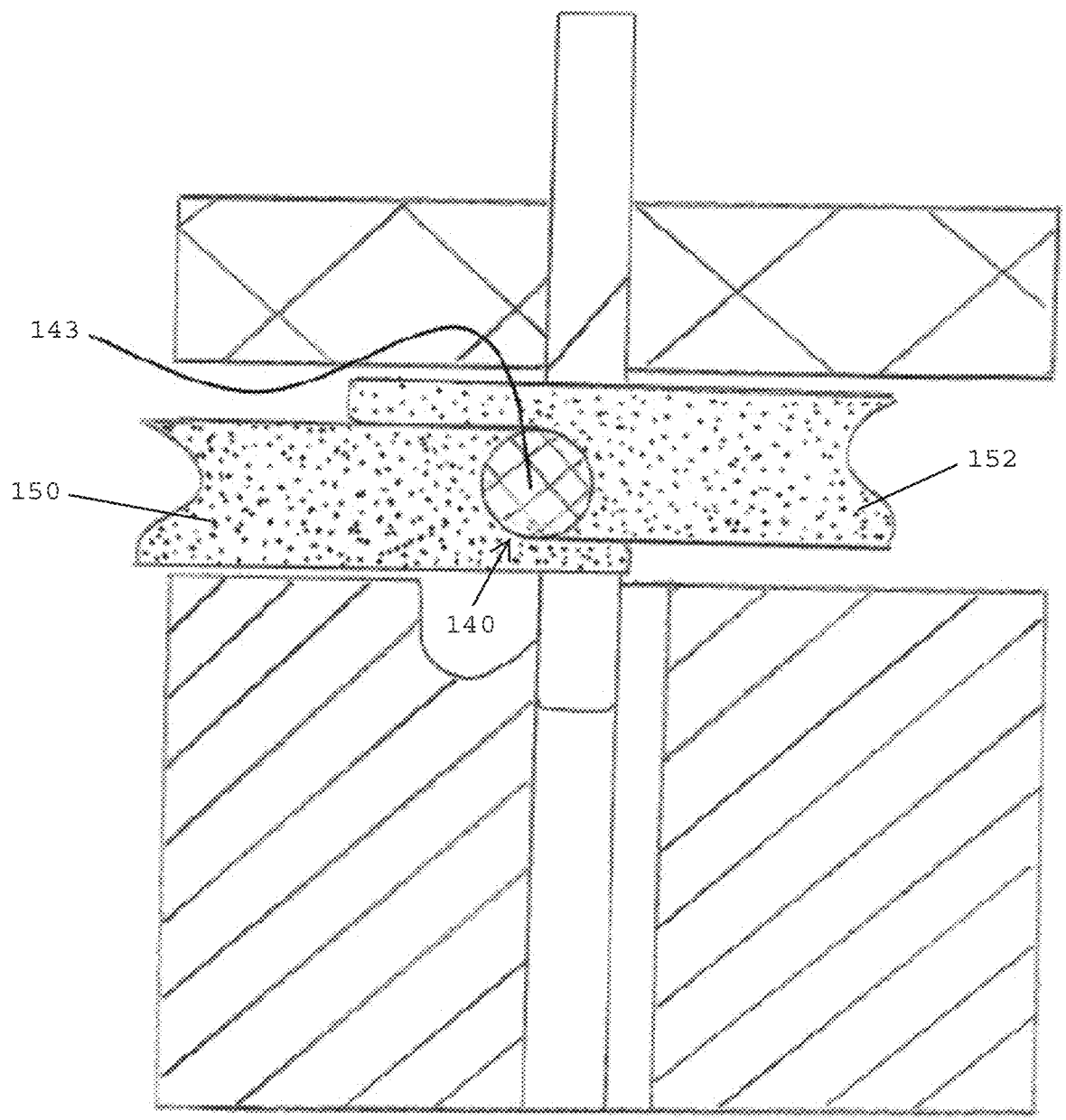
FIG. 5E shows a stage of a method of making a suture having a reformed, reduced diameter tip, in accordance with one embodiment of the present patent application.

Referring to FIG. 5E, in one embodiment, when the first and second reforming dies 150, 152 are closed, the core mass 143 of the suture 140 is reshaped and/or reformed between the opposing J-shaped forming faces. In one embodiment, the core mass 143 is desirably pressed and reshaped into a more circular and/or cylindrical profile by the first and second reforming dies 150, 152.

Figure 5F:
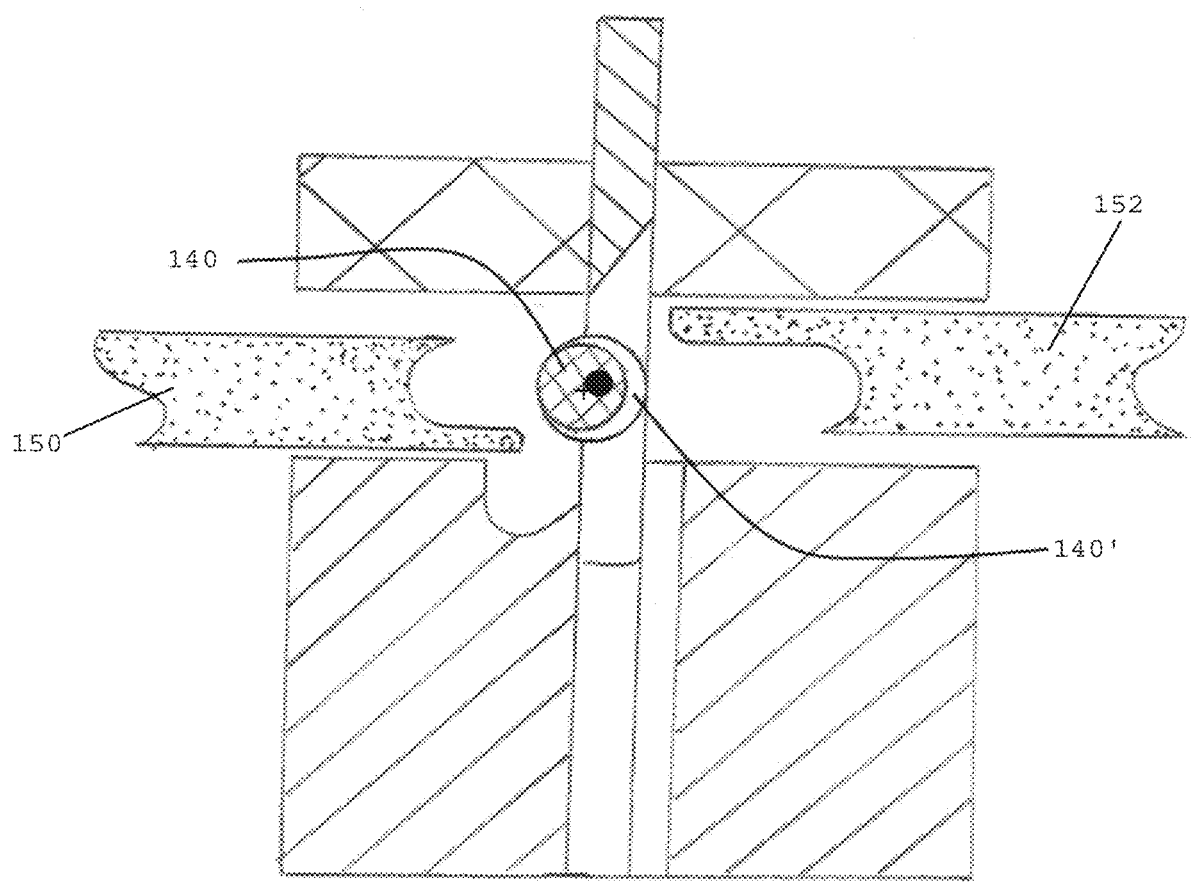
FIG. 5F shows a stage of a method of making a suture having a reformed, reduced diameter tip, in accordance with one embodiment of the present patent application.

Referring to FIG. 5F, in one embodiment, after the core mass 143 has been reformed, the first and second reforming dies 150, 152 may be retracted whereby the reformed core mass 143 of the suture 140 has a central axis (designated by a cross) that is not co-axial with the central axis (designated by a dot) of the original, uncut region of the suture 140.

The systems, devices, and methods disclosed herein may be used with any conventional monofilament suture. Examples of commercially available monofilament sutures that may be tipped using the systems, devices and methods disclosed herein include sutures sold under the trademarks PROLENE® suture, PRONOVA® suture, PDS® suture, NUROLON® suture, as well as surgical gut sutures, and stainless steel sutures and the like. The sutures may be made from conventional biocompatible polymeric materials, both synthetic and natural materials such as surgical gut. The sutures may be made from absorbable or non-absorbable polymers, or combinations thereof. The absorbable polymers include conventional biocompatible, polymers such as lactide, polylactic acid, polyglycolic acid, glycolide, polydioxanone, polycaproactone, copolymers and blends thereof and the like. The nonabsorbable polymers include conventional biocompatible polymers such as, polyolefinspolyamides (polyhexamethylene adipamide (nylon 66), polyhexamethylene sebacamide (nylon 610), polycapramide (nylon 6), polydodecanamide (nylon 12) and polyhexamethylene isophthalamide (nylon 61) copolymers and blends thereof), polyesters (e.g. polyethylene terephthalate, polybutyl terephthalate, copolymers and blends thereof), fluoropolymers (e.g. polytetrafluoroethylene and polyvinylidene fluoride), polyolefins (e.g., polypropylene including isotactic and syndiotactic polypropylene and blends thereof, as well as, blends composed predominately of isotactic or syndiotactic polypropylene blended with heterotactic polypropylene (such as are described in U.S. Pat. No. 4,557,264 issued Dec. 10, 1985 assigned to Ethicon, Inc. hereby incorporated by reference) and polyethylene including ultra high molecular weight polyethylene and the like and combinations thereof. The sutures may also be made from conventional biocompatible metals and metal alloys including surgical stainless steel, Nitinol, etc.

The tipped sutures disclosed herein may have suture sizes ranging from size 5 to size 10-0. In one embodiment, the tipped sutures disclosed herein may be mounted to conventional surgical needles made from conventional biocompatible materials such as metal alloys including surgical stainless steel, tungsten-rhenium alloys, etc. If desired, the surgical needles may be made from other biocompatible materials including ceramics, polymeric materials and composites, etc. The needles will preferably have proximal needle mounting ends having drilled bore holes or channeled features for receiving a distal suture tip and mounting it to the needle. The suture tips may be mounted or secured (i.e., attached) to the proximal suture mounting ends of the surgical needles by conventional attachment techniques including mechanical swaging, gluing, melting, etc. In one embodiment, the maximum outer dimension at the proximal mounting end of the needle after the suture tip has been mounted and secured (i.e., attached) in place will preferably be equal to the maximum diameter of the body of the needle.

Figure 6A:
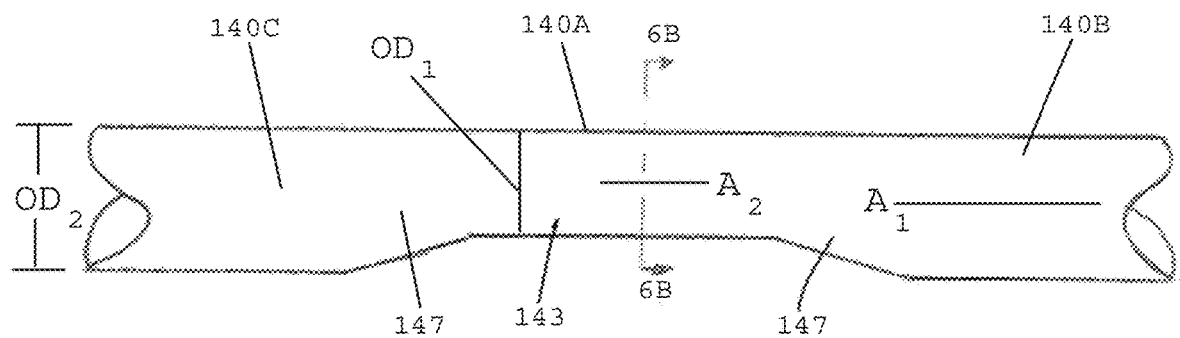
FIG. 6A shows a side view of a suture having larger diameter first and second ends and a reformed, reduced diameter tip located between the first and second ends, in accordance with one embodiment of the present patent application.
Figure 6B:
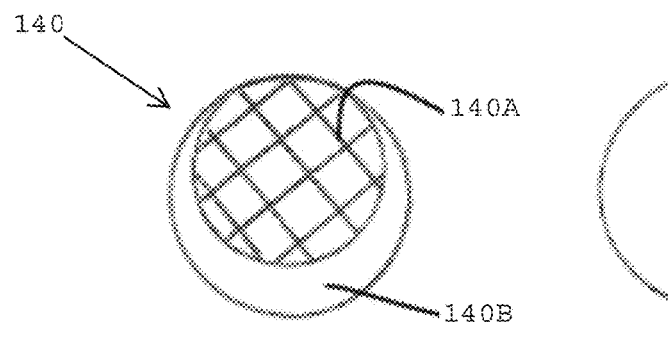
FIG. 6B shows a cross-sectional end view of the suture shown in FIG. 6A including the reformed, red cued diameter tip and the larger diameter first end.
Figure 6C:
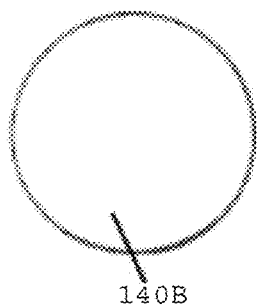
FIG. 6C shows a cross-sectional view of the larger diameter first end of the suture shown in FIGS. 6A and 6B.

Referring to FIGS. 6A-6C, after the core mass 143 within the center region 140A of the suture 140 has been reformed by the reforming die, the reformed mass 143 has a central axis $A_2$ that is not co-axial with the central axis $A_1$ of the unaltered first and second ends 140B, 140C of the suture 140. In one embodiment, the reformed mass 143 preferably includes a sloping transitional region 147 that defines a generally asymmetric conical structure that transitions from the smaller cross-sectional dimension $OD_1$ of the reformed mass 143 to the larger cross-sectional dimension $OD_2$ of the first and second ends 140B, 140C of the suture.

Figure 7A:
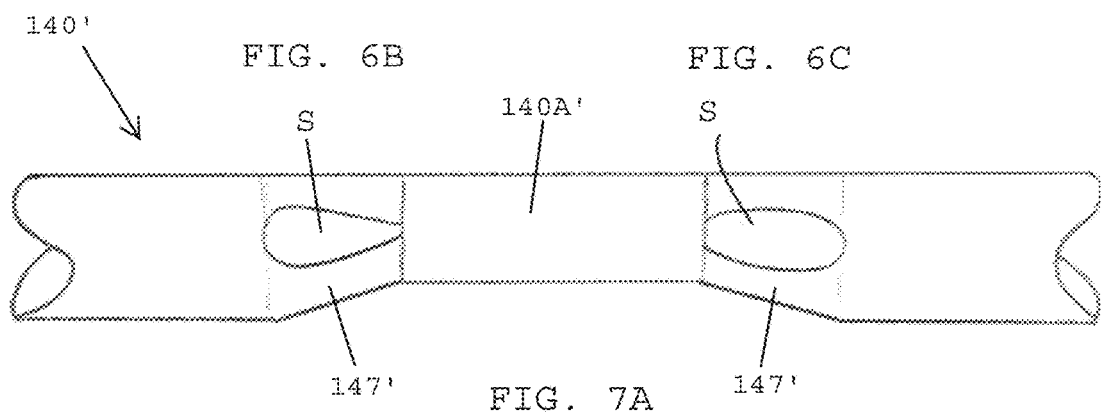
FIG. 7A shows a side view of a suture having larger diameter first and second ends and a reformed, reduced diameter tip located between the first and second ends, in accordance with one embodiment of the present patent application.
Figure 7B:
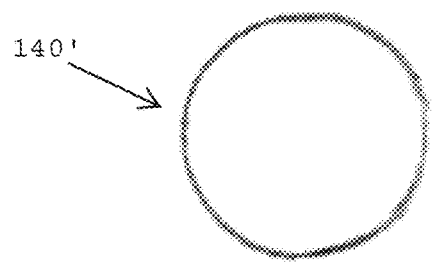
FIG. 7B shows a cross-sectional end view of the suture shown in FIG. 7A including the larger diameter first end.

Referring to FIGS. 7A and 7B, in one embodiment, a center region 140A' of the suture 140' that has been subjected to the reforming die creates a generally round profile in the center region. In this embodiment, the transition portions 147' of the suture are only partially reformed and segments S of the original trimmed surface remain.

Figure 8:
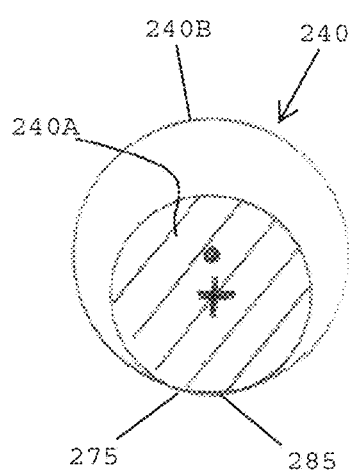
FIG. 8 shows a cross-sectional end view of a suture having a reformed, reduced diameter tip, in accordance with one embodiment of the present patent application.

In certain embodiments of the present patent application, the systems, devices and methods disclosed herein may be utilized to produce surgical sutures having various cross-sectional configurations. Referring to FIG. 8, in one embodiment, the reformed tip 240A of a suture 240 is not co-axial with the unaltered portion 240B of the suture, which is illustrated by the X mark for the central axis of the reformed tip 240A versus the dot for the central axis of the original, unaltered region 240B of the suture 240. In the embodiment shown in FIG. 8, the reformed tip 240A has one portion 275 of its outer perimeter that is aligned with a portion 285 of the outer perimeter of the original, unaltered region 240B of the suture.

Figure 9:
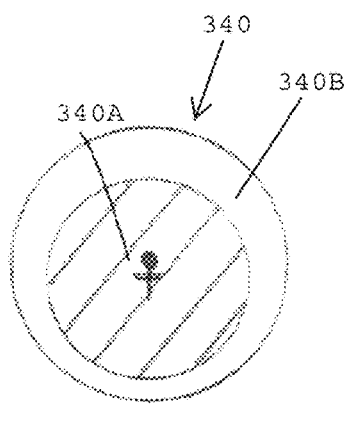
FIG. 9 shows a cross-sectional end view of a suture having a reformed, reduced diameter tip, in accordance with one embodiment of the present patent application.

Referring to FIG. 9, in one embodiment, the reformed tip 340A of a suture 340 is not co-axial with the unaltered portion 340B of the suture, which is illustrated by the X mark designating the central axis of the reformed tip 340A versus the dot designating the central axis of the unaltered portion 340B of the suture 340.

Figure 10:
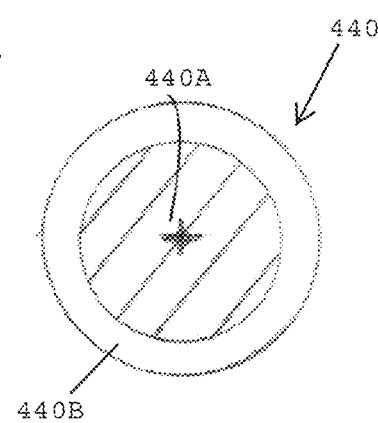
FIG. 10 shows a cross-sectional end view of a suture having a reformed, reduced diameter tip, in accordance with one embodiment of the present patent application.

Referring to FIG. 10, in one embodiment, the reformed tip 440A of a suture 440 is co-axial with the unaltered portion 440B of the suture, which is illustrated by the X mark designating the central axis of the reformed tip 440A being in alignment with the dot designating the central axis of the unaltered region 440B of the suture 440. The reformed tip 440A has an outer dimension that is smaller than the outer dimension of the unaltered region 440B of the suture.

Figure 11:
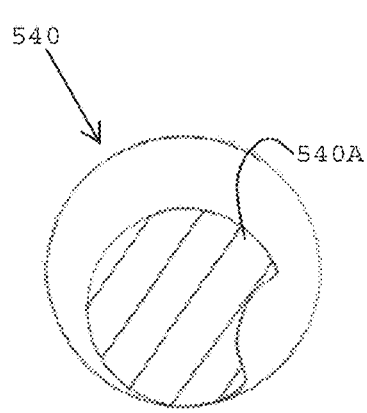
FIG. 11 shows a cross-sectional end view of a suture having a reformed, reduced diameter tip, in accordance with one embodiment of the present patent application.
Figure 12:
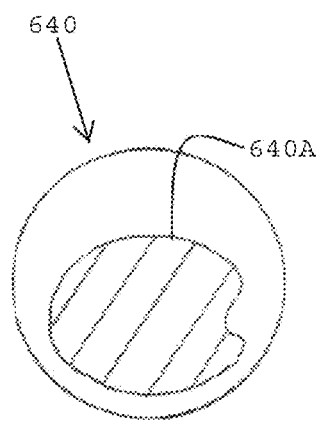
FIG. 12 shows a cross-sectional end view of a suture having a reformed, reduced diameter tip, in accordance with one embodiment of the present patent application.
Figure 13:
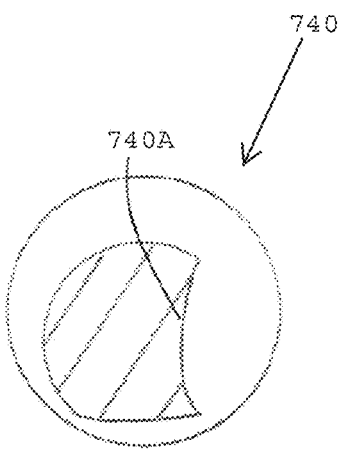
FIG. 13 shows a cross-sectional end view of a suture having a reformed, reduced diameter tip, in accordance with one embodiment of the present patent application.

Referring to FIGS. 11-13, in certain embodiments, other reformed shapes are feasible for the reduced diameter portions of the reformed tips 540A, 640A, and 740A of the respective suture 540, 640, 740. These different shapes may be achieved using reforming die having various geometries or through the partial closure of the reforming dies.

Figure 14A:
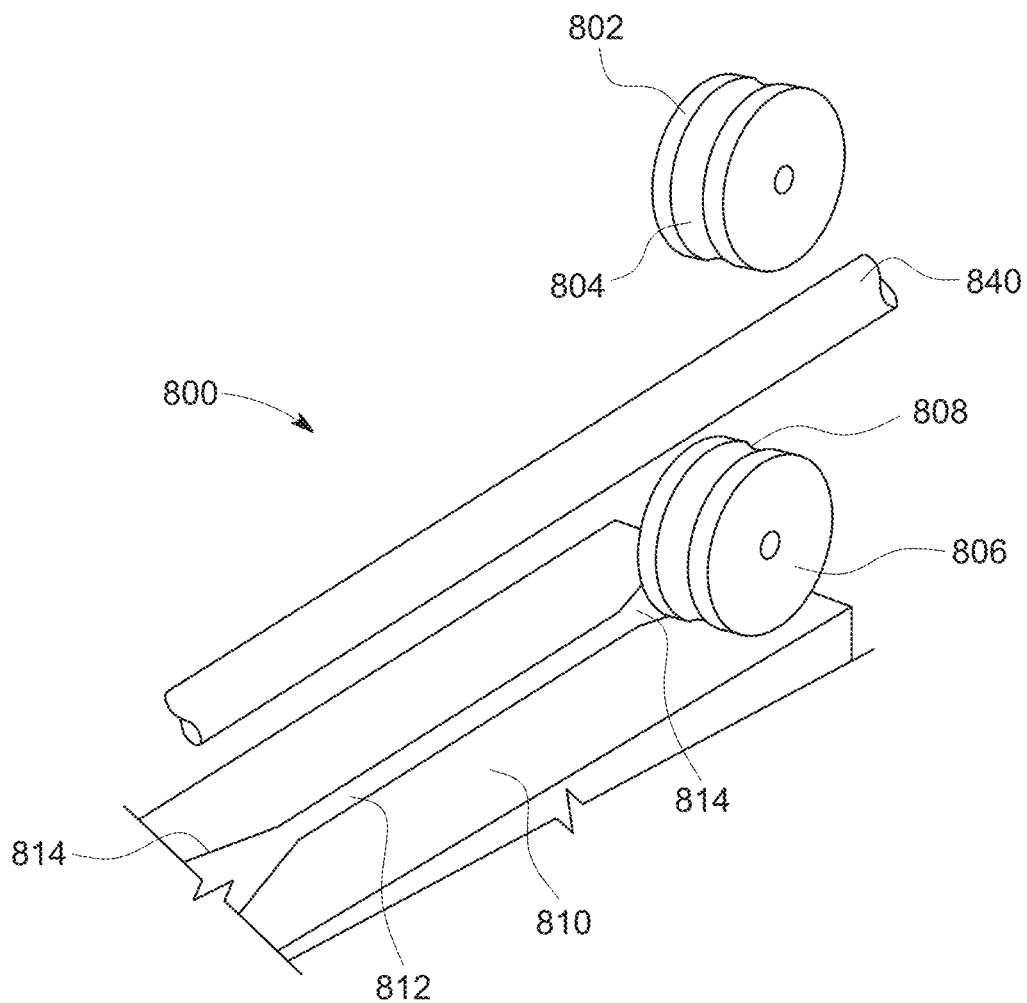
FIG. 14A shows a perspective view of a system for making sutures having reformed, reduced diameter tips including a first roller, a second roller, and a cutting die, in accordance with one embodiment of the present patent application.

Referring to FIG. 14A, in one embodiment, a system 800 for shaping a suture 840 to make sutures having reformed, reduced diameter tips preferably includes a first forming roller 802 having a groove 804, such as a concave groove, formed in the outer perimeter thereof, and a second forming roller 806 having a groove 808, such as a concave groove, formed in the outer perimeter thereof. In one embodiment, the first and second forming rollers 802, 806 may have uniform roll surfaces. In one embodiment, the first and second forming rollers 802, 806 may be driven and may be mounted on a frame that will bring the rollers into proximity about a suture 840 and that will traverse the rollers for a short distance over the outer surface(s) of the suture to reform the suture. The system 800 preferably includes a cutting die including a lower half of a cutting die 810 having a receiver slot 812 that is sized and shaped to match the desired final profile of the suture. The receiver slot 812 preferably includes tapered portions 814 at the opposing ends of the receiver slot 812. In one embodiment, a spring-loaded ejector element may be contained within the receiver slot 812 for ejecting a section of a suture as disclosed in commonly assigned US 2015/0351752 to Rousseau et al., the disclosure of which is hereby incorporated by reference herein.

Figure 14B:
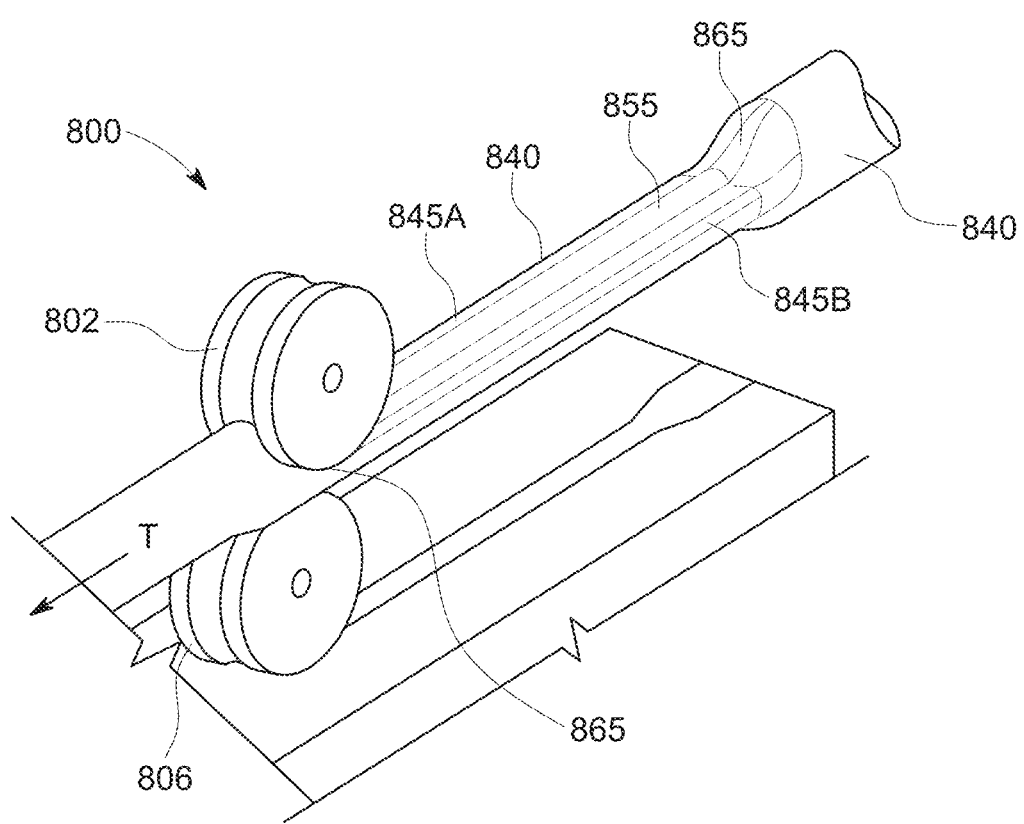
FIG. 14B shows the system of FIG. 14A as the first and second rollers engage an outer surface of a suture.

Referring to FIG. 14B, in one embodiment, the first and second forming rollers 802, 806 may be moved into proximity to each other so that they may traverse over a selected region 840A of the suture 840 as the respective rollers are driven about their respective central axes. As a result, the selected region 840A of the suture may be deformed to provide a suture having a pair of laterally extending wings 845A, 845B and arcuate shaped upper and lower surfaces 855. The sloping portions 865 of the suture at the initiation and termination points of roller contact preferably form a natural tapered transition region of displaced material.

Figure 15A:
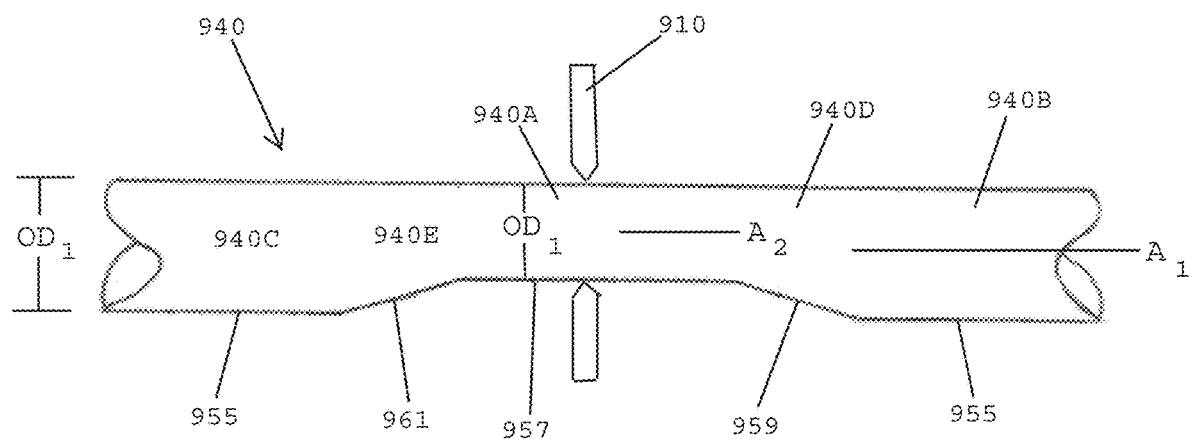
FIG. 15A shows a stage of a method of making a suture having a reformed, reduced diameter tip, in accordance with one embodiment of the present patent application.

Referring to FIG. 15A, in one embodiment, a surgical suture 940 may include an elongated fiber having a first end 940B, a second end 940C and a central axis $A_1$ that extends along the length of the elongated fiber, between the first and second ends 940B, 940C thereof. The first and second ends 940A, 940B of the elongated fiber have an outer surface 955 that defines an outer dimension $OD_1$. In one embodiment, the elongated fiber preferably has a reformed center region 940A, which is disposed between the first and second ends 940B, 940C. The reformed center region 940A shown in FIG. 15A has been subjected to the processing steps disclosed herein whereby a laterally extending deformed mass has been cut from the center region, and the remaining core mass has been reformed using reforming die. The reformed center region 940A of the elongated fiber 940 preferably defines a reduced diameter region of the elongated fiber having an outer surface 957 that defines an outer dimension $OD_2$ that is less than the $OD_1$ of the first and second ends 940A, 940B of the elongated fiber. In one embodiment, the reformed center region 940A has a length that extends along a central axis $A_2$ that is offset from the central axis $A_1$ of the first and second ends 940B, 940C of the elongated fiber.

In one embodiment, the elongated fiber has a first transition region 940D that preferably extends between the first end 940A and the center region 940A thereof. In one embodiment, the first transition region 940D has a sloping outer surface 959 that slopes inwardly between the outer surface 955 of the first end 940B of the fiber and the outer surface 957 of the reformed center region 940A of the fiber.

In one embodiment, the elongated fiber has a second transition region 940E that extends between the second end 940C and the center region 940A thereof. In one embodiment, the second transition region 940E has a sloping outer surface 961 that slopes inwardly between the outer surface 955 of the second end 940C of the fiber and the outer surface 957 of the center region 940A of the fiber.

Figure 15B:
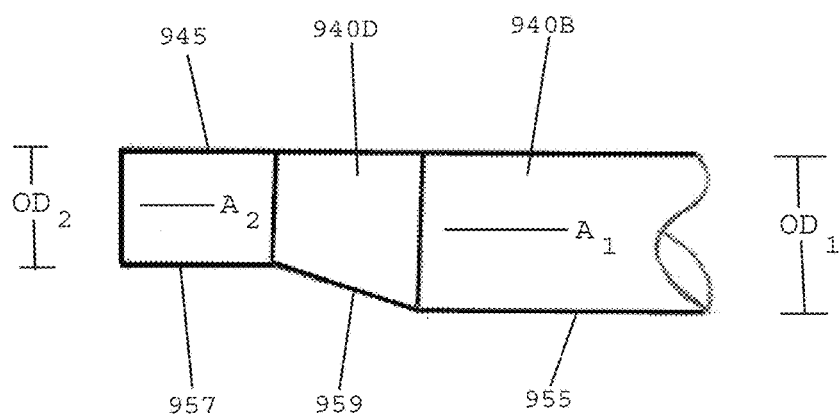
FIG. 15B shows a stage of a method of making a suture having a reformed, reduced diameter tip, in accordance with one embodiment of the present patent application.

Referring to FIGS. 15A and 15B, in one embodiment, the center region 940A of the elongated fiber may be cut using a cutting blade 910 for forming two separate sutures, each having a reformed, reduced diameter tip. In one embodiment, cutting the center region 940A will produce a first tipped suture that includes the first end 940B and a first section of the center region 940A (e.g., the section to the right of the cutting blade 910), and a separate, second suture that includes the second end 940C and a second section of the center region 940A (e.g., the section to the left of the cutting blade 910).

Referring to FIG. 15B, in one embodiment, a first suture 940 having a reformed, reduced diameter tip includes the first end 940B having an outer surface 955 that defines an outer diameter $OD_1$. The first end 940B has a length that extends along the central axis $A_1$. The reformed, reduced diameter tip 945 has an outer surface 957 that defines an outer diameter $OD_2$ that is less than $OD_1$. The reformed, reduced diameter tip 940A has a length that extends along a central axis $A_2$ that is offset from central axis $A_1$ of the first end 940B. The first suture has a sloping surface 959 that defines a transition region 940D that is located between the larger diameter first end 940B and the reduced diameter reformed tip 945.

Figure 16:
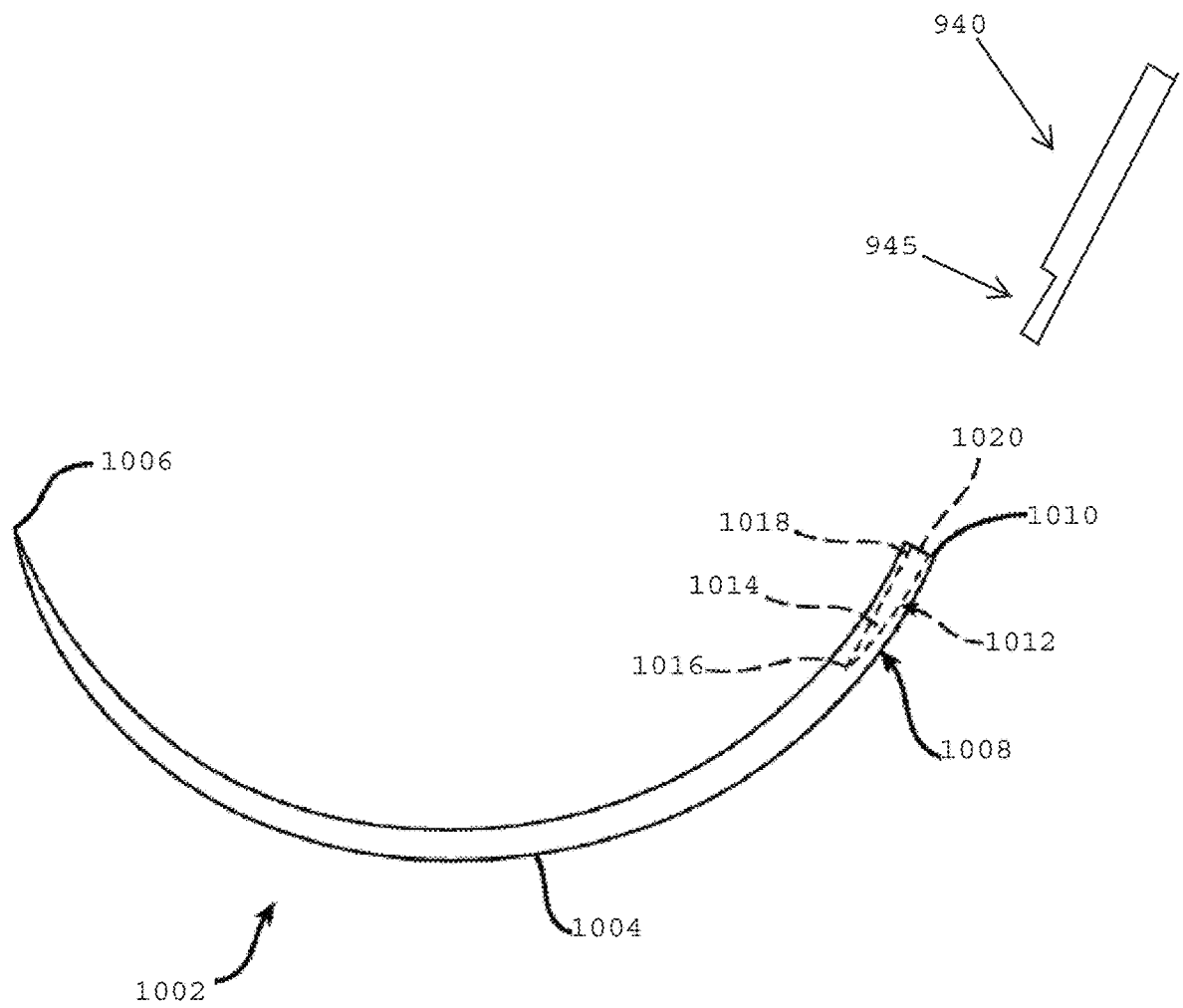
FIG. 16 shows a stage of a method of attaching a distal end of a suture having a reformed, reduced diameter tip to a proximal end of the surgical needle, in accordance with one embodiment of the present patent application.

Referring to FIG. 16, in one embodiment, the surgical suture 940 having the reformed, off-axis, reduced diameter tip 945 shown and described above in FIGS. 15A and 15B may be attached to a proximal end of a surgical needle 1002. In one embodiment, the surgical needle 1002 may be made from a biocompatible metal, such as a tungsten-rhenium refractory alloy. In one embodiment, the needle 1002 preferably has a body 1004 with a distal piercing point 1006 and a suture mounting section 1008 located adjacent the proximal end 1010 of the needle. A suture mounting bore hole 1012 may be at the proximal end of the needle. In one embodiment, the bore hole 1012 preferably includes a cavity 1014 having a distal end 1016 and a proximal end 1018 in communication with the opening 1020 formed at the proximal end 1010.

The needle 1002 may be made using conventional manufacturing processes that are adapted to manufacturing surgical needles made from biocompatible metals such as refractory metal alloys. Typically, in a conventional process, wire made from the desired metal alloy is drawn in a wire mill to a desired diameter. The wire is then cut in conventional wire cutting equipment to produce needle blanks having the desired length. The wire then goes through a series of conventional manufacturing process steps including forming, grinding, polishing, cleaning and drilling.

Needle blanks may be drilled in several ways. The blanks may be mounted in a fixture and a conventional mechanical drill may be used to drill out a bore hole in the proximal end of the needle blank. Although mechanical drilling may be useful to drill bore holes in surgical needles, there are limitations associated with such a drilling process. For example, drills wear out and need to be replaced on a constant basis. In addition, the mechanical drilling process is time consuming and is less desirable for high speed, automated production processes. In addition, mechanical drills cannot typically be used in a cost effective manner for drilling needles made from very hard materials, or those that readily work-harden during the drilling operation. Laser drilling systems have been developed for drilling bore holes in surgical needles. These laser systems typically use Nd:YAG lasers, but any laser type capable of providing the required power density and being focused to the required spot size would be acceptable. Specific cycles are utilized to obtain the desired bore hole diameter and depth by controlling laser beam parameters including beam power, energy density, energy density distribution, pulse shape, pulse duration, and the number of pulses.

Figure 17:
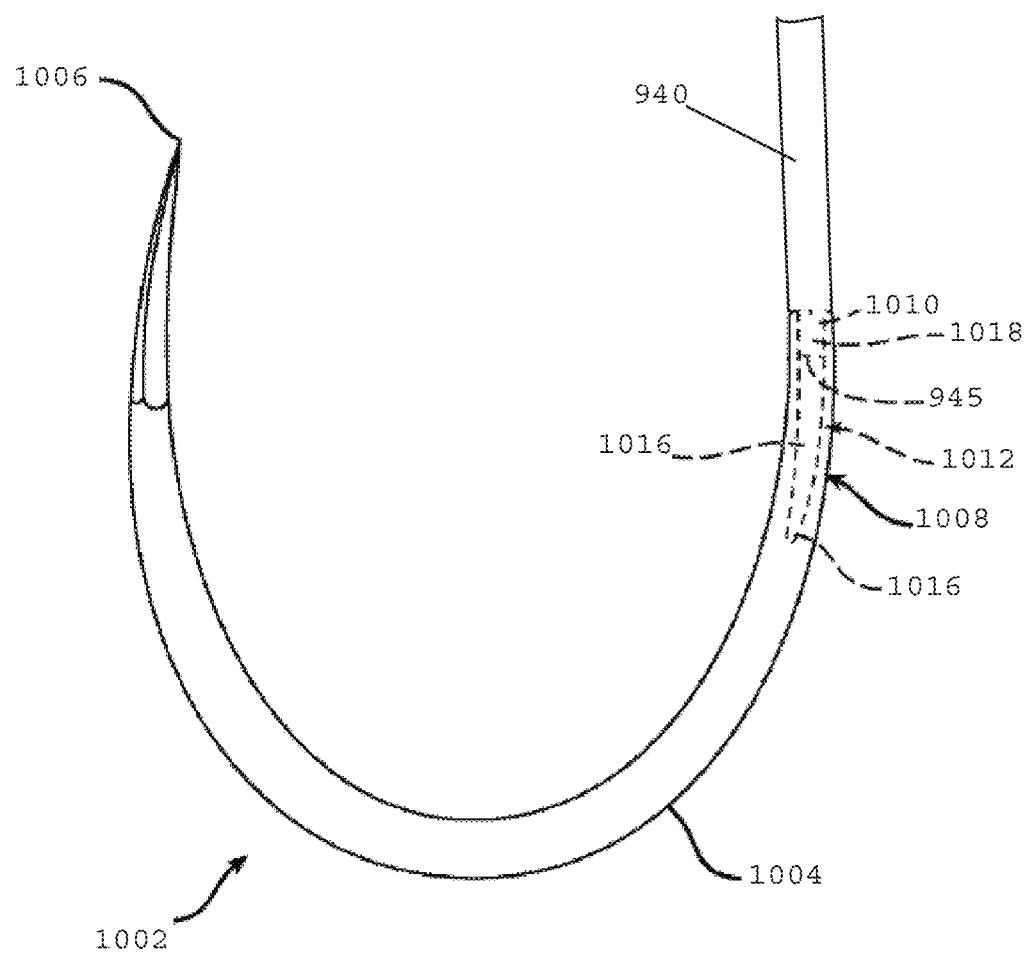
FIG. 17 shows the suture having the reformed, reduced diameter tip and the surgical needle of FIG. 16 after the distal end of the suture has been secured to the proximal end of the surgical needle, in accordance with one embodiment of the present patent application.

Referring to FIGS. 16 and 17, in one embodiment, the surgical suture 940 having the reformed tip 945 may be inserted into the bore hole 1012 having the opening 1020 at the proximal end 1010 of the surgical needle 1002. The surgical suture 1040 may be secured within the suture mounting section 1008 using a mechanical swaging die. In one embodiment, in order to swage the surgical suture 940 to the surgical needle 1002, the needle is mounted in the die and a tool is pressed against the suture mounting section 1008 of the needle. This causes a deformation of the metal such that the reformed tip 945 of the suture 940 that is inserted into the drilled bore hole 1012 is compressed within the cavity 1014 of the bore hole. Other methods for attaching the reformed tip of the suture to the proximal end of the surgical needle may include adhesive, glues and/or cements.

In one embodiment, during the cutting and reforming steps disclosed herein, heat, produced through resistance heaters, radio frequency generators, plasma, laser or ultrasonic equipment, may be utilized to assist in the mobilization of the polymer based structures to improve the cutting and/or forming operations.

In one embodiment, the systems, devices and methods disclosed herein may involve a manual process, whereby the elongated fiber is held in a fixed position within a clamping frame, or an automated spool feed type process.

In one embodiment of an automated spool feed process, a suture fiber to be tipped may be fed from a payout spool into a tip forming system. The leading end of the fiber may be positioned within an indexing head, which may draw the fiber into a heating and forming station. The heating and forming station may be configured with a set of forming dies similar to those disclosed herein. The dies may be mounted for vertical travel and may optionally be heated. Alternatively, the die may be run only in a cooled configuration. The heating of the fiber may be achieved through the use of a heating source that is located at the same axial position as the forming die station along the length of the suture. In one embodiment, the heating source may be positioned in a plane that is rotated 90 degrees relative to the plane of the forming station. For example, if the forming station traverses vertically, then the heating station may be mounted in the horizontal position to provide heating of the fiber while the fiber is positioned within the forming station. Heating sources may include but are not limited to conventional infrared heaters, heated convection mediums such as air streams, or other conductive sources such as heated dies, and the like and equivalents thereof.

In one embodiment, the systems, devices and methods for reforming a suture tip may use heat and/or pressure for shaping polymeric materials used to make elongated fibers. In one embodiment, the forming die may operate at a lower temperature than the heating source for reshaping the fiber while the die contact serves to cool the fiber during the forming step. In one embodiment, for materials that have a $T_g$ that is lower than room temperature, the heating of the material may not be necessitated and the forming operation may be conducted at ambient room temperature.

In one embodiment, the fiber may not be exposed to elevated tension during the cutting and reforming operations. In one embodiment, the fiber feeding mechanism may only advance the indexed amount of fiber through both the payout and take-up mechanism maintaining the same relative motion of the fiber.

In one embodiment, the systems, devices and methods disclosed herein produce surgical sutures having reformed tips that are dimensionally consistent and have an improved degree of precision that may not be attained when using bulk processing techniques such as extrusion or roll forming. The dimensional consistency enables repeatable attachment strengths when surgical needles are swaged onto the reformed suture tips. In certain embodiments, other features, such as indents, corrugations, opposing partial spirals or raised features, may be formed on the suture tip geometry, which may improve the needle attachment strength. Additionally, fiber fibrillation due to overdrawing of the fibers is avoided and the rigidity of the tipped fiber is not increased relative to the main body of the suture.

The novel process of the present can be utilized with surgical needles made from alloys of refractory metals including tungsten, molybdenum, niobium, tantalum, and rhenium. Surgical needles made from tungsten-rhenium alloys are disclosed in the following references which are incorporated by reference: U.S. Pat. No. 5,415,707 to Bendel et al., and U.S. patent application Ser. Nos. 11/611,353; 11/611,387; 11/756,668; and Ser. No. 11/756,679. In one embodiment, the systems, devices and methods disclosed herein may be used with laser drilled surgical needles made from conventional stainless steel alloys.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A system for making a surgical suture having a reformed tip, comprising:
   a receiver die having a top surface, a bottom surface, and an elongated channel formed in the top surface that extends between first and second ends of the receiver die;
   the elongated channel including a suture channel having a first end and a second end, a first sloping surface that extends downwardly between the first end of the suture channel and the first end of the receiver die, and a second sloping surface that extends downwardly between the second end of the suture channel and the second end of the receiver die;
   an upper die having a top surface and a bottom surface that opposes the top surface of the receiver die, wherein the system has an open die position in which the bottom surface of the upper die is spaced away from the top surface of the receiver die and a closed die position in which the bottom surface of the upper die is in contact with the top surface of the receiver die; and
   a cutting element coupled with the receiver die and the upper die.

2. The system as claimed in claim 1, further comprising:
   a cutting element guide slot that extends through the upper die and the receiver die along a cutting element movement axis that crosses the bottom surface of the upper die and the top surface of the receiver die; and
   the cutting element being adapted to slide within the cutting element movement axis of the cutting element guide slot in a first direction toward the top surface of the upper die and in a second direction toward the bottom surface of the receiver die.

3. The system as claimed in claim 1, wherein the suture channel comprises a suture seating surface that extends in a plane that is parallel with the top surface of the receiver die.

4. The system as claimed in claim 3, wherein the first sloping surface slopes downwardly between the first end of the suture channel and the bottom surface of the receiver die, and wherein the second sloping surface slopes downwardly between the second end of the suture channel and the bottom surface of the receiver die.

5. The system as claimed in claim 1, further comprising:
   the cutting element having an upper end, a lower end, a sharpened cutting edge located between the upper and lower ends of the cutting element, and first and second guide legs located on opposite ends of the sharpened cutting edge; and
   a suture reforming assembly including first and second reforming die having an extended position in which the first and second reforming die are joined together between the first and second guide legs of the cutting element and a retracted position in which the first and second reforming die are spaced from one another.

6. The system as claimed in claim 1, further comprising:
   a first cutting element guide slot formed in the upper die that extends from the top surface to the bottom surface of the upper die; and
   a second cutting element guide slot formed in the elongated channel of the receiver die, wherein the first and second cutting element guide slots are in alignment with one another, and wherein the cutting element is configured for sliding up and down within the first and second cutting element guide slots.

7. The system as claimed in claim 6, wherein the cutting element has an upper end, a lower end, a sharpened cutting edge located between the upper and lower ends of the cutting element, and first and second guide legs located on opposite ends of the sharpened cutting edge, and wherein the first and second guide legs are disposed within the second cutting element guide slot formed in the elongated channel of the receiver die for guiding up and down movement of the cutting element.

8. The system as claimed in claim 7, wherein the second cutting element guide slot has outer ends that are aligned with the first and second sloping surfaces of the elongated channel.

9. The system as claimed in claim 7, wherein the upper end is disposed with the first cutting element guide slot of the upper die.

10. The system as claimed in claim 7, wherein the cutting element has an angled blade that extends between the first and second guide legs of the cutting element.

* * * * *